US011903812B2

United States Patent
Balakrishnan

(10) Patent No.: US 11,903,812 B2
(45) Date of Patent: Feb. 20, 2024

(54) URETERAL STENT

(71) Applicant: MOZARC MEDICAL US LLC, Minneapolis, MN (US)

(72) Inventor: Aiswarya Balakrishnan, Galway (IE)

(73) Assignee: Mozarc Medical US LLC, Minneapolis, MN (US)

( * ) Notice: Subject to any disclaimer, the term of this patent is extended or adjusted under 35 U.S.C. 154(b) by 253 days.

(21) Appl. No.: 17/330,128

(22) Filed: May 25, 2021

(65) Prior Publication Data
US 2022/0378567 A1    Dec. 1, 2022

(51) Int. Cl.
*A61F 2/04*   (2013.01)

(52) U.S. Cl.
CPC .......... *A61F 2/04* (2013.01); *A61F 2002/048* (2013.01); *A61F 2230/005* (2013.01)

(58) Field of Classification Search
CPC .................. A61F 2/04; A61F 2002/048; A61F 2230/005; A61F 2/94; A61F 2/958; A61F 2220/0008; A61F 2220/0075; A61F 2250/0048; A61M 27/008
See application file for complete search history.

(56) References Cited

U.S. PATENT DOCUMENTS

| 6,887,215 B2 | 5/2005 | McWeeney |
| 8,021,434 B2 | 9/2011 | Segura et al. |
| 9,192,460 B2 | 11/2015 | Gandhi |
| 2007/0005122 A1* | 1/2007 | Inoue ........................ A61F 2/94 623/1.11 |
| 2008/0051911 A1* | 2/2008 | Rucker ..................... A61F 2/04 623/23.7 |

FOREIGN PATENT DOCUMENTS

JP    2016187366 A    * 11/2016

OTHER PUBLICATIONS

JP-2016187366-A Translation (Year: 2016).*

* cited by examiner

*Primary Examiner* — Brian A Dukert
*Assistant Examiner* — Rebecca Lynee Zimmerman

(57) ABSTRACT

In some examples, a medical system including a stent configured to be positioned within a ureter of a patient. The stent includes one or more distal petals and/or one or more proximal petals resiliently biased to deploy radially outwards from a stent body. The stent may be configured to position the distal petals in a kidney of a patient and position the proximal petals in a bladder of the patient. The distal petals and/or proximal petals may be configured to resist a migration of the stent within the ureter. The stent may include suture configured to cause the distal petals and/or proximal petals to substantially to collapse for withdrawal of the stent. The medical system may include a sheath to retain the distal petals and/or proximal petals in a collapsed condition during, for example, implantation in the patient.

20 Claims, 6 Drawing Sheets

URETERAL STENT

TECHNICAL FIELD

This disclosure is related to a stent configured to be positioned within a body passage, such as a ureteral stent configured to be positioned with a ureter.

BACKGROUND

The ureter is a passage in a body that allows urine to flow from the kidney to the bladder. In some urological conditions, obstructions and/or blockage of the ureter may develop, interfering with normal urinary flow from the kidney to the bladder. A ureteral stent may be positioned within the ureter in order to facilitate normal urinary drainage. Generally, the ureteral stent is positioned such that a distal end positions within a kidney and a proximal end positions in the vicinity of a ureteral orifice in the bladder. A lumen extending between the distal end and the proximal end provides a flow path from the kidney to the bladder. The ureteral stent may be employed to facilitate urinary drainage from the kidney to the bladder following the treatment and removal of stones, calculi, tumors, or other abnormalities of a ureter which interferes with normal urinary flow.

SUMMARY

This disclosure describes a medical system including a stent configured to be positioned within a ureter of a patient. The stent includes one or more distal petals and/or one or more proximal petals secured to a body of the stent. The distal petals and/or proximal petals are resiliently biased to extend outwards from the stent body to resist migration of the stent within the ureter. The stent may be configured to position the distal petals substantially in a kidney of the patient and position the proximal petals substantially in a bladder of the patient when the stent body is positioned within the ureter. When biased to extend outwardly from the stent body, the petals may function to secure or otherwise anchor the proximal and distal ends of the stent body in the bladder and kidney, respectively, e.g., by resisting axial motion of the stent body within the ureter. The stent may include one or more sutures attached to the distal petals and/or proximal petals that is configured to cause the distal petals and/or proximal petals to collapse when actuated (e.g., when a clinician exerts a force on the suture). The collapse of the petals may facilitate withdrawal of the stent from the patient. In examples, the medical system includes a sheath to temporarily retain the distal petals and/or proximal petals in a collapsed condition during, for example, implantation in the patient.

In an example, a medical system includes a stent, the stent comprising: a stent body defining a distal end and a proximal end, wherein the stent body is configured to be positioned in a ureter of a patient when the distal end is positioned substantially in a kidney of a patient and the proximal end is positioned substantially in a bladder of the patient; at least one distant petal attached to a distal portion of the stent body, wherein the at least one distal petal is resiliently biased to cause a portion of the at least one distal petal to displace away from an exterior surface of the stent body; and at least one proximal petal attached to a proximal portion of the stent body, wherein the at least one proximal petal is resiliently biased to cause a portion of the at least one proximal petal to displace away from the exterior surface of the stent body.

In an example, a medical system includes a stent, the stent comprising: a stent body defining a distal end and a proximal end, wherein the stent body is configured to be positioned in a ureter of a patient when the distal end positions substantially in a kidney of a patient and the proximal end positions substantially in a bladder of the patient, and wherein the stent body defines a proximal opening at the proximal end, a distal opening at the distal end, and a lumen extending from the proximal opening to the distal opening; at least one distant petal attached to a distal portion of the stent body, wherein the at least one distal petal is resiliently biased to cause a free end of the at least one distal petal to displace away from an exterior surface of the stent body, and wherein the at least one distal petal is configured to position substantially in the kidney when the distal end positions substantially in the kidney; and at least one proximal petal attached to a proximal portion of the stent body, wherein the at least one distal petal is resiliently biased to cause a free end of the at least one proximal petal to displace away from the exterior surface of the stent body, and wherein the at least one proximal petal is configured to position substantially in the bladder when the proximal end positions substantially in the bladder.

In an example, a method comprises: positioning a distal portion of a stent body of a stent and causing at least one distal petal attached to the distal portion to extend by using a resilient biasing of the at least one distal petal, wherein the resilient biasing causes a portion of the at least one distal petal to displace away from an exterior surface of the stent body, and wherein the stent body is configured to be positioned in a ureter of a patient when a distal end of the stent body positions substantially in a kidney of the patient and a proximal end of the stent body positions substantially in a bladder of the patient; and positioning a proximal portion of the stent body and causing at least one proximal petal attached to the proximal portion to extend by using a resilient biasing of the at least one proximal petal, wherein the resilient biasing causes a portion of the at least one proximal petal to displace away from the exterior surface of the stent body The details of one or more examples are set forth in the accompanying drawings and the description below. Other features, objects, and advantages will be apparent from the description and drawings, and from the claims.

DETAILED DESCRIPTION

Figure 1:
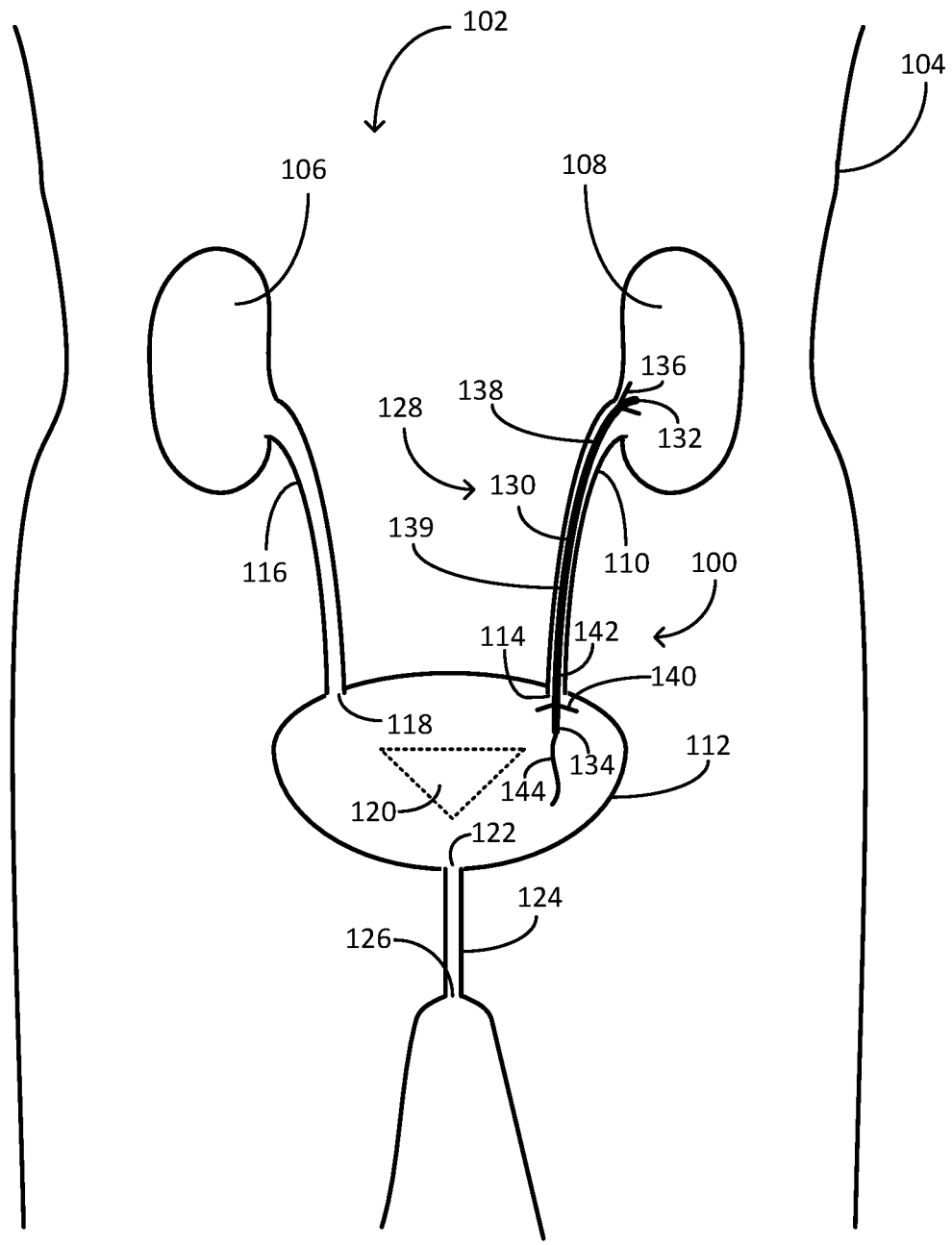
FIG. 1 is a schematic illustration of an example medical system including a stent positioned within a ureter of a patient.

The disclosure describes a medical system including a stent configured to be positioned within a ureter of a patient and techniques for using such a medical system. In some examples, the stent may be configured to facilitate urine flow from a kidney of the patient to a bladder of the patient. The stent may define a distal end configured to reside within the kidney of the patient and a proximal end configured to reside within the bladder of the patient when at least some portion of the stent is positioned within the ureter. A lumen defined by the stent ("stent lumen") extends between the distal end and the proximal end to facilitate urinary flow through the lumen from the kidney to the bladder. The stent includes one or more resiliently biased petals configured to accommodate movement of the patient while retaining the stent positioned within the ureter.

The medical system may be configured to substantially retain at least some portion of the stent within the ureter using one or more distal petals and/or one or more proximal petals. The one or more distal petals and/or one or more proximal petals may be resiliently biased to deploy radially outwards from a stent body. In examples, the stent is configured to position the one or more distal petals in a kidney of the patient and position the one or more proximal petals in a bladder of the patient when at least some portion of the stent is positioned in the ureter. When in a deployed position, the distal petals and/or proximal petals may be configured to substantially engage anatomical structures of the patient to limit migration of the stent within the ureter in the proximal and/or distal direction. The medical system may include a sheath configured to surround the stent and substantially maintain the distal petals and/or proximal petals collapsed against the stent body as the stent is positioned within the ureter (or transited through a urethra enroute to the ureter). The sheath may be proximally withdrawn from the ureter to cause the distal petals and/or proximal petals to deploy. In some examples, the stent includes a suture configured to exert a force on the distal petals and/or proximal petals causing the respective petals to collapse toward the stent body to, for example, facilitate withdrawal of the stent from the patient.

In some examples, the stent includes a stent body defining a distal end and a proximal end. The stent body may define a distal opening at the distal end and a proximal opening defined at the proximal end, and may define the stent lumen extending from the distal opening to the proximal opening. The stent includes at least one distal petal attached to a distal portion of the stent body and configured to retain the distal opening within or in the vicinity of the kidney when some portion of the stent is positioned within the ureter. The stent includes at least one proximal petal attached to a proximal portion of the stent body and configured to retain the proximal opening within or in the vicinity of a ureteral orifice opening to the bladder. The distal petal and the proximal petal may be resiliently biased to extend away from stent body to limit distal or proximal movements of the stent that might tend to cause migration within the ureter The distal petal and the proximal petal may be configured to engage anatomical structures of the patient when the stent experiences a distal or proximal movement within the ureter.

In examples, the medical system includes a sheath defining a lumen ("sheath lumen") configured to at least partially surround the stent. The sheath may be configured such that, when the sheath surrounds the stent, the sheath substantially maintains the distal petal and/or the proximal petal in a collapsed position substantially collapsed against the exterior surface of the sheath. Stated similarly, the sheath may be configured to overcome the resilient biasing of the distal petal and/or the proximal petal, such than an interior wall of the sheath lumen substantially maintains the distal petal free end and the proximal petal free end pressed against the exterior surface of the stent body. The sheath may be configured to at least partially position within the ureter of the patient when the sheath lumen surrounds the stent. The sheath may be configured such that the sheath may be proximally withdrawn while leaving the stent within the ureter. The resilient biasing of the distal petal and the proximal petal may cause some portion of (e.g., a free end of) the respective petals to substantially spring outward away from the stent body as the sheath is withdrawn, such that withdrawal of the sheath deploys the distal petal and the proximal petal to substantially retain the stent within the ureter of the patient.

In the deployed position, the one or more distal petals of the stent may be configured to limit and/or resist a proximal translation of the stent through the ureter once the stent is deployed within the ureter. In some examples, the distal petals, when in the deployed condition, are configured to limit and/or resist the proximal translation and substantially allow or provide less resistance to a distal translation of the stent through the ureter. In examples, a distal petal includes a fixed end ("distal petal fixed end") secured to the distal portion of the stent body and a free end ("distal petal free end") opposite the distal petal fixed end. The distal petal may be resiliently biased to displace the distal petal free end in a direction away from the stent body in the substantial absence of external forces acting on the distal petal. In examples, the distal petal is configured to position substantially within the kidney when the distal end of the stent body resides substantially within the kidney. The distal petal may be configured to engage an anatomical structure of the patient (e.g., a ureter orifice opening to the kidney) to resist a proximal translation of the stent body within the ureter when a proximal force is exerted on the stent body (e.g., due to patient movement). In examples, the stent includes a plurality of distal petals configured to extend radially outward from the stent body and acting to substantially increase the diameter of the stent body in the vicinity of the distal end. In examples, the plurality of distal petals are configured to define an increased diameter around the distal portion of the stent body at least exceeding the diameter of a ureter orifice opening to the kidney.

As described further below, one or more sutures may be attached to the distal and/or proximal petals. For example, a distal portion of a suture may be attached to a distal petal. The distal petal may be configured to substantially collapse toward the stent body (e.g., establish a collapsed position) when the suture exerts a force toward the stent body on the distal petal. In examples, the force exerted by the suture decreases a displacement between the distal petal free end and the stent body such that, for example, the stent may be withdrawn through the ureter by a clinician with a minimum or absence of interference between the distal petal and the ureter. In some examples, the distal petal is configured to substantially lie against an exterior surface of the stent body when the suture exerts the force toward the stent body. In some examples, the stent includes the suture. For example, the suture may be secured to the distal petal via a distal portion of the suture ("suture distal portion") and extend through the stent lumen such that a proximal portion of the suture ("suture proximal portion") extends through the proximal opening of the lumen. Hence, the stent may be configured such that clinician may exert a proximal force on the suture to substantially collapse the distal petal toward the stent body, such that the stent may be proximally withdrawn through the ureter of the patient.

In the deployed position, the one or more proximal petals of the stent may be configured to limit and/or resist a distal translation of the stent through the ureter once the stent is deployed within the ureter. In some examples, the proximal petals, when in the deployed position, are configured to limit and/or resist the distal translation and substantially allow or provide less resistance to a proximal translation of the stent through the ureter. A proximal petal may include a fixed end ("proximal petal fixed end") secured to the proximal portion of the stent body and a free end ("proximal petal free end") opposite the proximal petal fixed end. In examples, the proximal petal is resiliently biased to displace the proximal petal free end in a direction away from the stent body in the substantial absence of external forces acting on the proximal petal. The proximal petal may be configured to position substantially within the bladder when the proximal end of the stent body resides substantially within the bladder. In examples, the distal petal is configured to engage an anatomical structure of the patient (e.g., a ureter orifice opening to the bladder) to resist a distal translation of the stent body within the ureter when a distal force is exerted on the stent body (e.g., due to patient movement). In examples, the stent includes a plurality of proximal petals configured to extend radially outward from the stent body and acting to substantially increase the diameter of the stent body in the vicinity of the proximal end. In examples, the plurality of proximal petals are configured to define an increased diameter around the proximal portion of the stent body at least exceeding the diameter of a ureter orifice opening to the bladder.

A distal portion of a suture may be attached to a proximal petal. In some examples, the proximal petal is configured to substantially collapse toward the stent body (e.g., establish a collapsed position) when the suture exerts a force toward the stent body on the proximal petal. The suture exerting the force on the proximal petal may be the same suture secured to the distal petal or a different suture. In examples, exerted force decreases a displacement between the proximal petal free end and the stent body such that, for example, the stent may be withdrawn through a urethra of the patient with a minimum or absence of interference between the distal petal and the urethra. The proximal petal may be configured to substantially lie against the exterior surface of the stent body when the suture exerts the force on the proximal petal. The stent may include the suture secured to the proximal petal. Hence, the stent may be configured such that clinician may exert a proximal force on the suture to substantially collapse the proximal petal toward the stent body, such that the stent may be proximally withdrawn through the urethra of the patient.

In some examples, a suture includes a suture proximal portion defined by a suture body and a plurality of suture lengths each extending from the suture body and extending to a suture distal portions, such that the suture includes a plurality of suture distal portions. The suture may be configured such that the suture proximal portion extends through the proximal opening of the stent lumen (e.g., into the bladder of the patient) and at least one of the suture distal portions is secured to each of the proximal petals and/or distal petals of the stent. In this manner, the suture may be configured such that a single proximal force exerted on the suture proximal portion (e.g., by a clinician) may cause each of the proximal petals and/or distal petals to collapse toward the stent body, such that the stent may be proximally withdrawn through the ureter and/or urethra of the patient.

Hence, the medical system may be configured to substantially retain a stent within a ureter of a patient using one or more distal petals and one or more proximal petals resiliently biased to deploy radially outwards from a stent body. The stent may be configured to position the one or more distal petals in a kidney of the patient and position the one or more proximal petals in a bladder of the patient when some portion of the stent is positioned in the ureter. The distal petals and/or proximal petals may be configured to substantially engage anatomical structures of the patient to limit migration of the stent within the ureter. The medical system may include a sheath configured to surround the stent and substantially maintain the distal petals and/or proximal petals collapsed against the stent body when the stent is positioned within the ureter. The sheath may be proximally withdrawn to cause the distal petals and/or proximal petals to deploy. In examples, the stent includes a suture configured to exert a force toward the stent body on the distal petals and/or proximal petals, such that the stent may be withdrawn from the patient.

FIG. 1 is a schematic illustrating an example medical system 100 within a portion of a urinary tract 102 of a patient 104. FIG. 1 illustrates a right kidney of patient 104 as kidney 106 and a left kidney of patient 104 as kidney 108. A ureter 110 of patient 104 defines a fluid flow pathway for urine to flow from kidney 108 to a bladder 112 of patient 104 via a ureteral orifice 114 of patient 104 opening into bladder 112. A ureter 116 of patient 104 defines a fluid flow pathway for urine to flow from kidney 106 to bladder 112 via a ureteral orifice 118 of patient 104 opening into bladder 112. A trigone region 120 of bladder 112 is located generally ureteral orifices 114, 118 and an internal urethral orifice 122. Urethra 124 extends between internal urethral orifice 122 and external urethral orifice 126. Kidney 106, kidney 108, ureter 110, bladder 112, ureteral orifice 114, ureter 116, ureteral orifice 118, trigone region 120, internal urethral orifice 122, urethra 124, and external urethral orifice 126 are anatomical structures of patient 104.

Normally, urine flows from kidneys 106, 108 to bladder 112 through the respective passages of ureters 110, 116. In certain urological conditions, obstructions and/or blockage of a ureter passage may develop, interfering with normal urinary flow from kidney 106 or kidney 108 to the bladder 112. Obstruction and/or blockage of a ureter passage may occur due to, for example, a tumor on the ureteral wall, passage of a kidney stone, a ureterocele, ureteral fibrosis, endometriosis, an infection, and other causes. A ureteral stent may be positioned within one of ureters 110, 116 in order to facilitate normal urinary drainage from one of kidneys 106, 108 to bladder 112.

FIG. 1 illustrates a stent 128 of medical system 100 implanted within ureter 110 to facilitate urinary flow from kidney 108 to bladder 112. Stent 128 includes a body 130 ("stent body 130") extending between and defining a distal end 132 ("stent distal end 132") and a proximal end 134 ("stent proximal end 134") opposite stent distal end 132. Stent body 130 may define a stent lumen (not shown) extending between and opening to stent distal end 132 and stent proximal end 134. Stent 128 is configured to locate stent distal end 132 substantially within kidney 108 and locate stent proximal end 134 substantially within bladder 112 when some portion of stent body 130 is implanted within ureter 110. Stent 128 is configured such that urine may enter the stent lumen through the opening substantially at stent distal end 132 within kidney 108 and exit the stent lumen through the opening substantially at stent proximal end 134 within bladder 112. In some examples, stent body 130 may define one or more side accesses defining a passage from the stent lumen through stent body 130 to enhance drainage. Hence, stent 128 may be configured to substantially restore urinary flow from kidney 108 to bladder 112 when a urological condition results in obstructions and/or blockage of ureter 110.

Stent 128 is configured to substantially limit and/or resist a distal and/or proximal migration of stent 128 caused by, for example, movements of patient 104 while stent 128 is positioned within ureter 110, or other causes. For example, stent 128 may be configured to limit and/or resist a proximal migration of stent 128 tending to displace stent body 130 further toward bladder 112. In examples, stent 128 includes one or more distal petals such as distal petal 136 configured to substantially limit and/or resist the proximal translation. Distal petal 136 may be attached to a distal portion 138 of stent body 130 ("stent distal portion 138"). In examples, distal petal 136 is configured to extend outward from stent body 130 (e.g., establish a deployed condition) to increase an effective cross-sectional dimension of stent distal portion 138. Distal petal 136 may be configured to increase the effective cross-sectional dimension of stent distal portion 138 as the cross-sectional dimension of medial portion 139 of stent body 130 ("stent medial portion 139") within ureter 110 remains substantially unchanged. In examples, the increased cross-sectional dimension of stent distal portion 138 causes distal petal 136 to engage anatomical structures of patient 104 when stent body 130 migrates proximally within ureter 110, such that distal petal 136 limits and/or resists the proximal migration.

Distal petal 136 may be resiliently biased to cause distal petal 136 to define the effective cross-sectional dimension of stent distal portion 138 when, for example, distal petal 136 is substantially unconstrained (e.g., substantially free of external forces acting on distal petal 136). In examples, distal petal 136 is resiliently biased to cause some portion of distal petal 136 (e.g., a free end) to displace from stent body 130 in a direction away from stent body 130. The resilient biasing of distal petal 136 may cause distal petal 136 (e.g., a free end of distal petal 136) to expand radially outward from stent body 130 to increase the effective cross-sectional dimension of stent distal portion 138.

Stent 128 may be configured to limit and/or resist a distal migration of stent 128 tending to displace stent body 130 further toward kidney 108. In examples, stent 128 includes one or more proximal petals such as proximal petal 140 configured to substantially limit and/or resist the distal migration. Proximal petal 140 may be attached to a proximal portion 142 of stent body 130 ("stent proximal portion 142"). In examples, proximal petal 140 may be configured to extend outward from stent body 130 (e.g., establish a deployed condition) to increase an effective cross-sectional dimension of stent proximal portion 142. Proximal petal 140 may be configured to increase the effective cross-sectional dimension of stent proximal portion 142 as the cross-sectional dimension of stent medial portion 139 within ureter 110 remains substantially unchanged. In examples, the increased cross-sectional dimension of stent proximal portion 142 causes proximal petal 136 to engage anatomical structures of patient 104 when stent body 130 migrates distally within ureter 110, such that proximal petal 140 limits and/or resists the distal migration.

Proximal petal 140 may be resiliently biased to cause proximal petal 140 to define the effective cross-sectional dimension of stent proximal portion 142 when, for example, proximal petal 140 is substantially unconstrained (e.g., substantially free of external forces acting on proximal petal 140). In examples, proximal petal 140 is resiliently biased to cause some portion of proximal petal 140 (e.g., a free end) to displace from stent body 130 in a direction away from stent body 130. The resilient biasing of proximal petal 140 may cause proximal petal 140 (e.g., a free end of proximal petal 140) to expand radially outward from stent body 130 to increase the effective cross-sectional dimension of stent proximal portion 142.

Hence, stent 128 may be configured to substantially limit and/or resist a distal and/or proximal migration of stent 128 when implanted within ureter 110 of patient 104. In examples, stent 128 includes distal petal 136 configured to increase the effective cross-sectional dimension of stent distal portion 138, such that distal petal 136 limits and/or resists a proximal migration of stent body 130 toward bladder 112. In examples, stent 128 includes proximal petal 140 configured to increase the effective cross-sectional dimension of stent proximal portion 142, such that proximal petal 140 limits and/or resists a distal migration of stent body 130 toward kidney 108. Stent 128 may include any number of distal petals configured similarly to distal petal 136 and may include any number of proximal petals configured similarly to proximal petal 140. In some examples, stent distal portion 138 includes a plurality of distal petals arranged substantially symmetrically around a longitudinal axis defined by the lumen of stent 128. In some examples, stent proximal portion 142 includes a plurality of proximal petals arranged substantially symmetrically around a longitudinal axis defined by the lumen of stent 128.

Stent 128 may be implanted within ureter 110 of patient 104 by a clinician through urethra 124 and/or ureter 110. For example, the clinician may insert a guide wire into urethra 124 and advance the guide wire through bladder 112 and ureter 110 until a distal end of the guide wire is within kidney 108. The clinician may slide stent 128 distally over the guide wire through urethra 124, bladder 112, and ureter 110 until stent distal end 132 positions substantially within kidney 108 and stent proximal end 134 positions substantially within bladder 112. The clinician may use a pusher or other insertion tool to cause stent 128 to slide distally over the guide wire. In examples, the clinician may evaluate the position of stent 128 relative to ureter 110 using a cystoscope or other imaging modality configured to produce images of stent 128 and anatomical structures of patient 104 when stent 128 is positioned within patient 104.

In examples, medical system 100 includes a delivery sheath (not shown in FIG. 1) defining a sheath lumen. The sheath may be configured such that the sheath lumen surrounds at least some portion of stent body 130. In examples, stent 128 is configured to translate (e.g., slidably translate) at least distally relative to the sheath when the sheath lumen surrounds stent body 130. Stent 128 may be implanted by positioning stent 128 within the sheath lumen of the sheath such that distal petal 136 and/or proximal petal 140 are substantially constrained from radial expansion by a lumen wall of the sheath lumen (e.g., such that distal petal 136 and/or proximal petal 140 are in the collapsed position). The sheath and stent 128 may then be translated over the guide wire guide wire to position both the sheath and stent 128 within ureter 110. When stent 128 is positioned within ureter 110 (e.g., when stent distal end 132 is substantially within kidney 108 and/or stent proximal end 134 is substantially within bladder 112), the sheath may be proximally withdrawn relative to stent 128. The proximal withdrawal of the sheath may release distal petal 136 and allow the resilient biasing of distal petal 136 to cause distal petal 136 (e.g., a free end of distal petal 136) to displace radially outward from stent body 130 (e.g., to establish a deployed position), such that distal petal 136 limits a proximal translation of sheath 128 within ureter 110. Further proximal withdrawal of the sheath may release proximal petal 140 and allow the resilient biasing of proximal petal 140 to cause proximal petal 140 (e.g., a free end of proximal petal 140) to displace radially outward from stent body 130 (e.g., to establish a deployed position), such that proximal petal 140 limits a distal translation of sheath 128 within ureter 110.

Stent 128 may be configured such that distal petal 136 and/or proximal petal 140 may collapse toward stent body 130 from the radially expanded condition to, for example, allow stent 128 to be proximally withdrawn (e.g., by a clinician) from ureter 110. In examples, stent 128 includes a suture 144 configured to exert a force on distal petal 136 and/or proximal petal 140 to cause distal petal 136 and/or proximal petal 140 to substantially collapse inward toward stent body 130 (e.g., to cause distal petal 136 and/or proximal petal 140 establish a collapsed position). Stent 128 may be configured such that a clinician may exert a force on suture 144 (e.g., a proximal force), causing suture 144 to transmit the force to distal petal 136 and/or proximal petal 140 and causing distal petal 136 and/or proximal petal 140 to collapse toward stent body 130. In examples, stent 128 is configured to position a proximal end of suture 144 within bladder 112, urethra 124, or outside of patient 104. In some examples, suture 144 is configured to transfer a proximal force to stent body 130 sufficient to cause a proximal withdrawal of stent body 130 from ureter 110, such that a clinician may proximally withdraw stent 128 by exerting a proximal force on suture 144.

As used herein, when a distal petal (e.g., distal petal 136) displaces and/or extends from stent body 130 and/or a stent exterior surface of stent 128 (e.g., in a deployed position), this may refer to the distal petal positioning or being positioned to cause a separation (e.g. a space) between a portion of the distal petal and the stent body 130 and/or the stent exterior surface. The portion of the distal petal may be a free end of the distal petal, a body of the distal petal, or some other portion of the distal petal. In examples, the portion of the distal petal (e.g., a free end) displaces and/or extends from stent body 130 and/or the stent exterior surface while another portion of the distal petal (e.g., a fixed end) is secured to stent body 130 and/or the stent exterior surface.

When a proximal petal (e.g., proximal petal 140) displaces and/or extends from stent body 130 and/or a stent exterior surface of stent 128 (e.g., ni a deployed position), this may refer to the proximal petal positioning or being positioned to cause a separation (e.g. a space) between a portion of the proximal petal and the stent body 130 and/or the stent exterior surface. The portion of the proximal petal may be a free end of the proximal petal, a body of the proximal petal, or some other portion of the proximal petal. In examples, the portion of the proximal petal (e.g., a free end) displaces and/or extends from stent body 130 and/or the stent exterior surface while another portion of the proximal petal (e.g., a fixed end) is secured to stent body 130 and/or the stent exterior surface.

Figure 2:
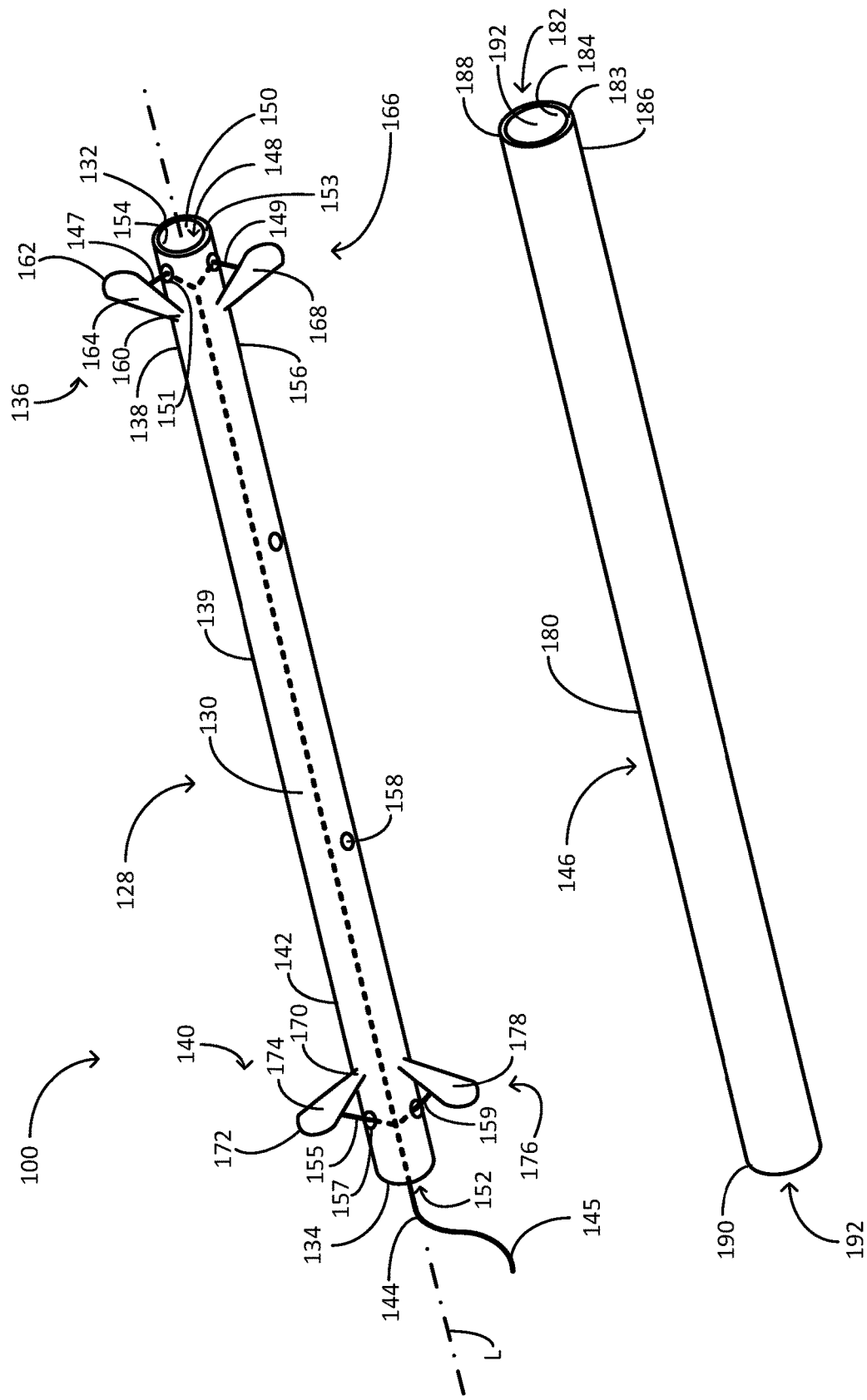
FIG. 2 is a conceptual perspective view of the medical system if FIG. 1 including a sheath.

FIG. 2 illustrates a perspective view of an example medical system 100 including stent 128 and a sheath 146. Stent body 130 may define a lumen 148 ("stent lumen 148") extending between an opening 150 substantially at stent distal end 132 ("stent distal opening 150") and an opening 152 substantially at stent proximal end 134 ("stent proximal opening 152"). Stent body 130 may include a wall 153 ("stent wall 153") defining an interior surface 154 ("stent interior surface 154") an exterior surface 156 ("stent exterior surface 156") opposite stent interior surface 154. Stent interior surface 154 may define stent lumen 148. Stent body 130 may define a longitudinal axis L extending through stent proximal opening 152 and stent distal opening 150. In examples, longitudinal axis L passes through stent lumen 148. Stent body 130 may define stent distal portion 138 including stent distal end 132, stent proximal portion 142 including stent proximal end 134, and stent medial portion 139 between stent distal portion 138 and stent proximal portion 142.

Stent 128 is configured such that urine may enter stent distal opening 150 from kidney 108 (FIG. 1) and flow through stent lumen 148 to exit into bladder 112 via stent proximal opening 152. In examples, stent body 130 defines one or more side accesses such as side access 158 which define a passage from stent lumen 148 and through stent wall 153 to enhance drainage, although this is not required. Stent body may be configured such that, when stent distal end 132 is positioned substantially within kidney 108 (FIG. 1) and stent proximal end 134 is positioned substantially within bladder 112, stent body 130 positions side access 158 within ureter 110. Further, although stent 128 and longitudinal axis L is depicted in substantially linear shapes in FIG. 2 for illustration, stent 128 and longitudinal axis L may assume other shapes in other examples, such as curved and curvilinear shapes. Stent 128 may be configured to curve and/or bend to, for example, accommodate anatomical passages of patient 104.

Stent 128 includes distal petal 136 configured to displace in a direction away from stent exterior surface 156 to increase a cross-sectional dimension (e.g., a cross-sectional dimension perpendicular to longitudinal axis L) of stent distal portion 138. Distal petal 136 may be secured to stent distal portion 138 and configured to extend outward away from stent exterior surface 156 to increase the cross-sectional dimension. In examples, distal petal 136 includes a fixed end 160 ("distal petal fixed end 160") secured to stent body 130 (e.g., exterior surface 156), a free end 162 ("distal petal free end 162") opposite distal petal fixed end 160, and a body 164 ("distal petal body 164") extending between distal petal fixed end 160 and distal petal free end 162. In examples, distal petal 136 is configured to cause distal petal free end 162 to displace in a direction away from stent exterior surface 156 when distal petal fixed end 160 is secured to stent exterior surface 156. Distal petal 136 may be configured to cause distal petal free end 162 to displace away from stent exterior surface 156 to increase the cross-sectional dimension of stent distal portion 138. In examples, distal petal 136 is configured to cause a displacement substantially perpendicular to longitudinal axis L between stent exterior surface 156 and distal petal 136 (e.g., distal petal free end 162). Stent 128 may be configured such that the increased cross-sectional dimension caused by the extension of distal petal 136 reduces and/or eliminates a proximal migration of stent 128 within ureter 110 (FIG. 1). Stent 128 may be configured such that the increased cross-sectional dimension caused by distal petal 136 reduces and/or eliminates a proximal migrations of stent 128 caused by movement or motions of patient 104). In some examples, the resilient biasing of distal petal 136 is sufficient to cause distal petal 136 to substantially maintain a deployed position when an anatomical structure exerts a force against distal petal 136 as a result of an axial force on stent 128 caused by movements of patient 104.

Stent 128 may one or more distal petals configured to increase the cross-sectional dimension of stent distal portion 138. In examples, stent 128 includes a plurality of distal petals 166 ("distal petals 166") including at least distal petal 136 and a distal petal 168. Each distal petal in the plurality may be configured to define a displacement between a portion of the distal petal and stent exterior surface 156, such that collectively distal petals 166 define a maximum cross-sectional dimension of stent distal portion 138. In examples, a distal petal is secured to stent body 130 around at least some portion (e.g., a fractional portion or substantially all) of a periphery defined by stent body 130.

Stent 128 may include proximal petal 140 configured to displace in a direction away from stent exterior surface 156 to increase a cross-sectional dimension (e.g., a cross-sectional dimension perpendicular to longitudinal axis L) of stent proximal portion 142. Proximal petal 140 may be secured to stent proximal portion 142 and configured to extend outward away from stent exterior surface 156 to increase the cross-sectional dimension. For example, proximal petal 140 may include a fixed end 170 ("proximal petal fixed end 170") secured to stent body 130 (e.g., exterior surface 156) and a free end 172 ("proximal petal free end 172") opposite proximal petal fixed end 170. Proximal petal 140 may include a body 174 ("proximal petal body 174") extending between proximal petal fixed end 170 and proximal petal free end 172. Proximal petal 140 may be configured to cause proximal petal free end 172 to displace in a direction away from stent exterior surface 156 when proximal petal fixed end 170 is secured to stent exterior surface 156. Proximal petal 140 may be configured to cause proximal petal free end 172 to displace away from stent exterior surface 156 to increase the cross-sectional dimension of stent proximal portion 142. In examples, proximal petal 136 is configured to cause a displacement substantially perpendicular to longitudinal axis L between stent exterior surface 156 and proximal petal 140 (e.g., proximal petal free end 172). Stent 128 may be configured such that the increased cross-sectional dimension caused by the extension of proximal petal 140 reduces and/or eliminates a distal migration of stent 128 within ureter 110 (FIG. 1). Stent 128 may be configured such that the increased cross-sectional dimension caused by proximal petal 140 reduces and/or eliminates a distal migrations of stent 128 caused by movement or motions of patient 104). In some examples, the resilient biasing of proximal petal 140 is sufficient to cause proximal petal 140 to substantially maintain a deployed position when an anatomical structure exerts a force against proximal petal 140 as a result of an axial force on stent 128 caused by movements of patient 104.

Stent 128 may include one or more proximal petals configured to increase the cross-sectional dimension of stent proximal portion 142. In examples, stent 128 includes a plurality of proximal petals 176 ("proximal petals 176") including at least proximal petal 140 and a proximal petal 178. Each proximal petal in the plurality may be configured to define a displacement between a portion of the proximal petal and stent exterior surface 156, such that collectively proximal petals 176 define a maximum cross-sectional dimension of stent proximal portion 142. In examples, a proximal petal is secured to stent body 130 around at least some portion (e.g., a fractional portion or substantially all) of a periphery defined by stent body 130.

Individual petals within distal petals 166 and/or proximal petals 176 may be resiliently biased to cause some portion of the individual petal to displace from stent exterior surface 156. For example, distal petal 136 may be resiliently biased to cause some portion of distal petal 136 to extend away from stent exterior surface 156 to increase the effective cross-sectional dimension of stent distal portion 138. In examples, the resilient biasing of distal petal 136 results in a tendency of distal petal 136 to return or attempt to return to an initial position relative to stent exterior surface 156 when distal petal 136 is temporarily displaced from the initial position by a force toward or away from stent exterior surface 156. For example, distal petal 136 may be configured such that an initial displacement between a portion of distal petal 136 (e.g., distal petal free end 162 and/or distal petal body 164) and stent exterior surface 156 decreases when a force acts on distal petal 136 in a direction toward stent exterior surface 156. Distal petal 136 may be resiliently biased such that, when the force acting on distal petal 136 is removed, distal petal 136 returns to a position relative to stent exterior surface 156 that substantially re-establishes the initial displacement. In some examples, distal petal 136 is configured to substantially maintain the initial displacement when distal petal 136 is in a substantially zero-stress position, where any stresses on distal petal 136 arise from properties or phenomena internal to distal petal 136, such as mass, internal temperature, residual stresses, and the like. In examples, distal petal 136 includes a shape-memory material such as a shape-memory metal or shape-memory polymer configured to resiliently bias distal petal 136 to extend away from stent exterior surface 156.

Any given distal petal in distal petals 166 (e.g., distal petal 168) and/or proximal petals 176 (e.g., proximal petal 140, 178) may be resiliently biased in a similar manner to that described for distal petal 136. Hence, distal petals 166 and/or proximal petals 176 may be configured to substantially spring outward under the influence of resilient biasing once stent 128 is implanted within ureter 110, in order to limit migration of stent 128 within ureter 110 (FIG. 1). Distal petals 166 and/or proximal petals 176 may be configured to displace toward stent exterior surface 156 to reduce a cross-sectional dimension of stent 128 as stent 128 is removed (e.g., by a clinician) from patient 104.

Further, although FIG. 2 depicts distal petals 166 generally oriented such that a free end of a distal petal is distally displaced from a fixed end of the distal petal, such an orientation is not required. In examples, distal petals 166 may include one or more distal petals oriented such that the distal petal free end is proximally displaced from the distal petal fixed end, or displaced from the distal petal fixed end in some other direction. In like manner, although FIG. 2 depicts proximal petals 176 generally oriented such that a free end of a proximal petal is proximally displaced from a fixed end of the proximal petal, this orientation is not required. In examples, proximal petals 176 may include one or more proximal petals oriented such that the proximal petal free end is distally displaced from the proximal petal fixed end, or displaced from the proximal petal fixed end in some other direction.

As shown in FIG. 2, e.g., stent 128 may include a suture 144 configured to selectively cause distal petals 166 and/or proximal petals 176 to decrease a cross-sectional dimension of stent 128. Suture 144 may be configured to extend at least partially through stent lumen 148. In FIG. 2, portions of suture 144 extending through stent lumen 148 are represented as dashed lines.

Suture 144 may be configured to selectively reduce a cross-sectional dimension of stent distal portion 138 and/or stent proximal portion 142. Suture 144 may be configured to reduce the cross-sectional dimension of stent 128 to, for example, facilitate withdrawal (e.g., by a clinician) of stent 128 through ureter 110, bladder 112, and urethra 124 of patient 104 (FIG. 1). In examples, suture 144 defines a proximal portion 145 ("suture proximal portion 145") configured such that exertion of a force on suture proximal portion 145 (e.g., by a clinician "pulling" on the proximal portion 145) causes distal petals 166 and/or proximal petals 176 to decrease a cross-sectional dimension of stent 128. In some examples, suture 144 is configured such that when stent 128 is positioned within ureter 110 (FIG. 1), suture proximal portion 145 extends into bladder 112 to allow a clinician to exert the force on suture proximal portion 145 to decrease the cross-sectional dimension and facilitate withdrawal of stent 128 from patient 104.

Suture 144 may be configured to exert a force on stent distal portion 138, stent proximal portion 142, or both stent distal portion 138 and stent proximal portion 142. In examples, suture 144 is configured to exert a force on at least one of distal petals 166 to cause an extending distal petal to deflect toward stent exterior surface 156 to reduce the cross-sectional dimension of stent distal portion 138. In some examples, suture 144 is configured to exert a force on each of distal petals 166 to cause each distal petal to deflect toward stent exterior surface 156 to reduce the cross-sectional dimension of stent distal portion 138. In examples, suture 144 may be configured to exert a force one at least one of proximal petals 176 to cause an extending proximal petal to deflect toward stent exterior surface 156 to reduce the cross-sectional dimension of stent proximal portion 142. In some examples, suture 144 is configured to exert a force on each of proximal petals 176 to cause each proximal petal to deflect toward stent exterior surface 156 to reduce the cross-sectional dimension of stent proximal portion 142.

As an example, suture 144 may extend from suture proximal portion 145 through stent lumen 148 to a distal portion 147 ("suture distal portion 147") mechanically engaged with distal petal 136. Suture 144 may be configured to transmit a proximal force (e.g., a pulling force) exerted on suture proximal portion 145 through suture 144 to cause suture distal portion 147 to exert at last some portion of the force on distal petal 136. The force exerted on distal petal 136 may decrease the displacement between distal petal 136 and stent body 130 caused by the resilient biasing of distal petal 136. In examples, the force exerted on distal petal 136 causes some portion of distal petal 136 (e.g., distal petal free end 162 and/or distal petal body 164) to displace toward stent exterior surface 156. The force exerted on distal petal 136 by suture distal portion 147 may overcome the resilient biasing of distal petal 136 to cause distal petal 136 to displace toward stent exterior surface 156. In some examples, distal petal 136 is configured to substantially lie against stent exterior surface 156 when the suture distal portion 147 exerts the force on distal petal 136. Hence, stent 128 may be configured such that clinician may exert a force (e.g., a proximal force) on suture proximal portion 145 to substantially collapse distal petal 136 toward stent body 130 to decrease a cross-sectional dimension of stent distal portion 138.

Suture 144 may be configured in any manner to cause suture distal portion 147 to mechanically engage distal petal 136. In examples, suture 144 extends at least partially through stent lumen 148 and suture distal portion 147 exits stent lumen 148 to mechanically engage distal petal 136. In some examples, stent body 130 defines a suture access 151 configured to allow suture distal portion 147 to pass from stent lumen 148 (e.g., through stent wall 153) and mechanically engage distal petal 136. Suture access 151 may be configured as a passage opening to and extending between stent interior surface 154 and stent exterior surface 156.

In some examples, suture 144 includes a plurality of distal portions. For example, suture 144 may include at least suture distal portion 149 in addition to suture distal portion 147. Suture 144 may be configured to transmit some portion of a proximal force (e.g., a pulling force) exerted on suture proximal portion 145 to suture distal portion 149. In examples, suture distal portion 149 is mechanically engaged with distal petal 168. Distal petal 168, suture distal portion 149, suture 144, and suture proximal portion 145 may be configured individually and in relation to each other in the same manner as that described for distal petal 136, suture distal portion 147, suture 144, and suture proximal portion 145. Hence, a proximal force (e.g., a pulling force) exerted on suture proximal portion 145 may cause suture distal portion 149 to exert at last some portion of the force on distal petal 168 and cause distal petal 168 to decrease the displacement between distal petal 168 and stent body 130. Thus, in some examples, stent 128 may be configured such that a single force (e.g., a pulling force) exerted on suture proximal portion 145 (e.g., by a clinician) may cause both distal petal 136 and distal petal 168 to displace toward stent body 130 to decrease a cross-sectional dimension of stent distal portion 138. Suture 144 may include any number of distal ends configured to transmit a force to cause any number of distal petals to displace toward stent body 130.

Suture 144 may be configured to exert a force on stent proximal portion 142 in addition to or instead of stent distal portion 138 to reduce a cross-sectional dimension of stent distal portion 138. In examples, suture 144 is configured to extend from suture proximal portion 145 through stent lumen 148 to a suture distal portion 155 mechanically engaged with proximal petal 140. Suture 144 may be configured to transmit a proximal force (e.g., a pulling force) exerted on suture proximal portion 145 through suture 144 to cause suture distal portion 155 to exert at last some portion of the force on proximal petal 140 to, for example, decrease the displacement between proximal petal 140 and stent body 130. The force exerted on proximal petal 140 may cause some portion of proximal petal 140 (e.g., proximal petal free end 172 and/or proximal petal body 174) to displace toward stent exterior surface 156. The force exerted on proximal petal 140 by suture distal portion 155 may overcome the resilient biasing of proximal petal 140 to cause proximal petal 140 to displace toward stent exterior surface 156. In some examples, proximal petal 140 is configured to substantially lie against stent exterior surface 156 when the suture distal portion 155 exerts the force on proximal petal 140.

Suture 144 may be configured in any manner to cause suture distal portion 155 to mechanically engage proximal petal 140. In examples, suture distal portion 155 exits stent lumen 148 (e.g., through suture access 157) to mechanically engage distal petal 136. Suture access 157 may be configured as a passage opening to and extending between stent interior surface 154 and stent exterior surface 156.

Suture 144 may include at least suture distal portion 159 in addition to suture distal portion 155, suture distal portion 147, and/or suture distal portion 149. Suture 144 may be configured to transmit some portion of a proximal force (e.g., a pulling force) exerted on suture proximal portion 145 to suture distal portion 159. Suture distal portion 149 may be mechanically engaged with proximal petal 178. Proximal petal 178, suture distal portion 159, suture 144, and suture proximal portion 145 may be configured individually and in relation to each other in the same manner as that described for proximal petal 140, suture distal portion 155, suture 144, and suture proximal portion 145. Hence, a proximal force (e.g., a pulling force) exerted on suture proximal portion 145 may cause suture distal portion 155 to exert at last some portion of the force on proximal petal 178 and cause proximal petal 178 to decrease the displacement between proximal petal 178 and stent body 130. Stent 128 may be configured such that a single force (e.g., a pulling force) exerted on suture proximal portion 145 (e.g., by a clinician) may cause both proximal petal 140 and proximal petal 178 to displace toward stent body 130 to decrease a cross-sectional dimension of stent distal portion 138.

In some examples, suture 144 is configured such that a single force (e.g., a pulling force) exerted on suture proximal portion 145 (e.g., by a clinician) causes substantially all of distal petals 166 and proximal petals 176 to displace toward stent body 130, such that the single force reduces a cross-sectional dimension of both stent distal portion 138 and stent proximal portion 142. For example, as depicted in FIG. 2, suture 144 may include suture distal portion 147, suture distal portion 149, suture distal portion 155, and suture distal portion 159, with suture proximal portion 145 configured to transmit a proximal force to each of suture distal portion 147, suture distal portion 149, suture distal portion 155, and suture distal portion 159. Thus, a single force exerted on suture proximal portion 145 (e.g., by a clinician) may cause suture 144 to transmit a first portion of the single force to suture distal portion 147, a second portion of the single force to suture distal portion 149, a third portion of the single force to suture distal portion 155, and a fourth portion of the single force to suture distal portion 159. The respective portions may cause suture distal portion 147 to displace distal petal 136 toward stent body 130, suture distal portion 149 to displace distal petal 168 toward stent body 130, suture distal portion 155 to displace proximal petal 140 toward stent body 130, and suture distal portion 159 to displace proximal petal 178 toward stent body 130. Hence, stent 128 may be configured such that a single force exerted on suture proximal portion 145 both causes distal petals 166 to decrease a cross-sectional dimension of stent distal portion 138 and causes proximal petals 176 to decrease a cross-sectional dimension of stent proximal portion 142.

In examples, medical system 100 includes sheath 146. Sheath 146 may be configured to cause distal petals 166 and/or proximal petals 176 to displace toward stent exterior surface 156 to, for example, reduce the cross-sectional dimensions of stent 128 during an implantation. Sheath 146 may be configured to surround stent body 130 such that sheath 146 substantially maintains distal petals 166 and/or proximal petals 176 substantially collapsed against stent exterior surface 156. Sheath 146 may be configured to overcome the resilient biasing of distal petals 166 and/or proximal petals 176 to substantially maintain distal petals 166 and/or proximal petals 176 pressed against stent exterior surface 156 when sheath 146 surrounds stent body 130.

Sheath 146 may include a body 180 ("sheath body 180") defining a lumen 182 ("sheath lumen 182") sized and shaped so that a least a portion of stent body 130 may be inserted within lumen 182, e.g., so that body 180 at least partially surrounds stent body 130. In examples, sheath body 180 includes a wall 183 ("sheath wall 183") defining an interior surface 184 ("sheath interior surface 184") and an exterior surface 186 ("sheath exterior surface 186") opposite sheath interior surface 184. Sheath interior surface 184 may define sheath lumen 182. Sheath body 180 may define an distal end 188 ("sheath distal end 188") and a proximal end 190 ("sheath proximal end 190") opposite sheath distal end 188. Sheath body 180 may define a distal opening 192 ("sheath distal opening 192") opening to sheath lumen 182 at sheath distal end 188, and may define a proximal opening 194 ("sheath proximal opening 194") opening to sheath lumen 182 at sheath proximal end 190.

Sheath lumen 182 may be configured such that stent body 130, distal petals 166, and/or proximal petals 176 may positioned within sheath lumen 182. Sheath lumen 182 may be configured such that sheath interior surface 184 overcomes the resilient biasing of distal petals 166 and/or proximal petals 178 to position distal petals 166 and/or proximal petals 178 substantially pressed against stent exterior surface 156 when stent body 130, distal petals 166 and/or proximal petals 178 position within sheath lumen 182. In examples, sheath lumen 182 is be configured such that stent body 130, distal petals 166, and/or proximal petals 176 may translate (e.g., distally and/or proximally) relative to sheath 146 when stent body 130, distal petals 166, and/or proximal petals 176 are positioned within sheath lumen 182. At least sheath distal opening 192 may be configured to allow stent body 130, distal petals 166, and/or proximal petals 176 to pass distally therethrough from a position within sheath lumen 182. In examples, sheath proximal opening 194 may be configured to allow stent body 130, distal petals 166, and/or proximal petals 176 to pass proximally therethrough from a position within sheath lumen 182.

Figure 3:
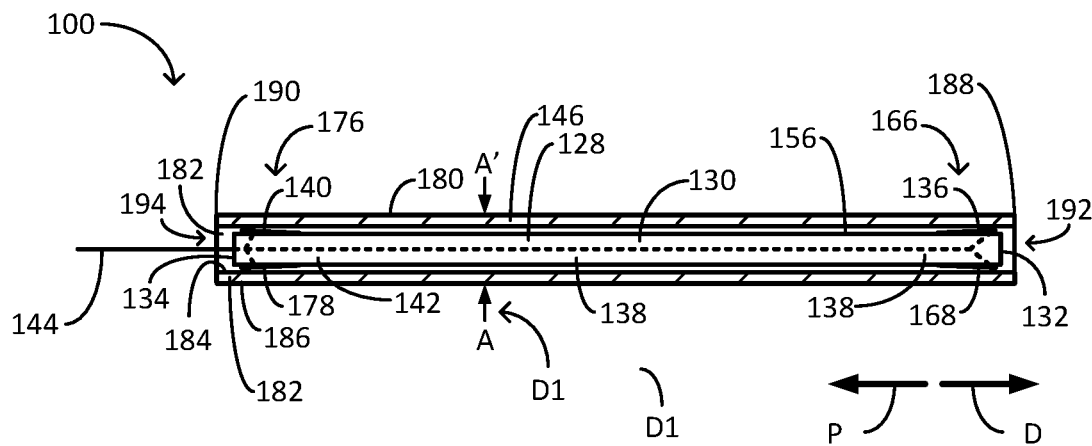
FIG. 3 is a schematic illustration of the medical system of FIG. 1 and FIG. 2 including the stent within the sheath.

As an example, FIG. 3 schematically illustrates medical system 100 with stent 128 (e.g., stent body 130, distal petals 166, and proximal petals 176 positioned within sheath 146. Sheath 146 is illustrated in an axial cross-section for clarity. Sheath interior surface 184 is overcoming the resilient biasing of distal petals 166 (e.g., distal petal 136, 168) and proximal petals 176 (e.g., proximal petal 140, 178), such that distal petals 166 and proximal petals 176 are substantially collapsed inward against stent exterior surface 156 (e.g., such that distal petals 166 and proximal petals 176 are in a collapsed position). Hence, stent 128 is positioned within sheath lumen 182 such that sheath 146 and stent 128 (e.g., stent body 130, distal petals 166, and proximal petals 176) are bound by (e.g., confined within) an outer boundary defined by sheath exterior surface 186. Sheath exterior surface 186 may define the outer boundary to have a maximum cross-sectional dimension D1 (e.g., a diameter) sufficient to allow sheath 146 and the enclosed stent 128 to be transited through urethra 124 and bladder 112 for positioning (e.g., by a clinician) within ureter 110 of patient 104 (FIG. 1). The maximum cross-sectional dimension D1 is represented as the displacement between arrow A and arrow A' in FIG. 3.

Figure 4:
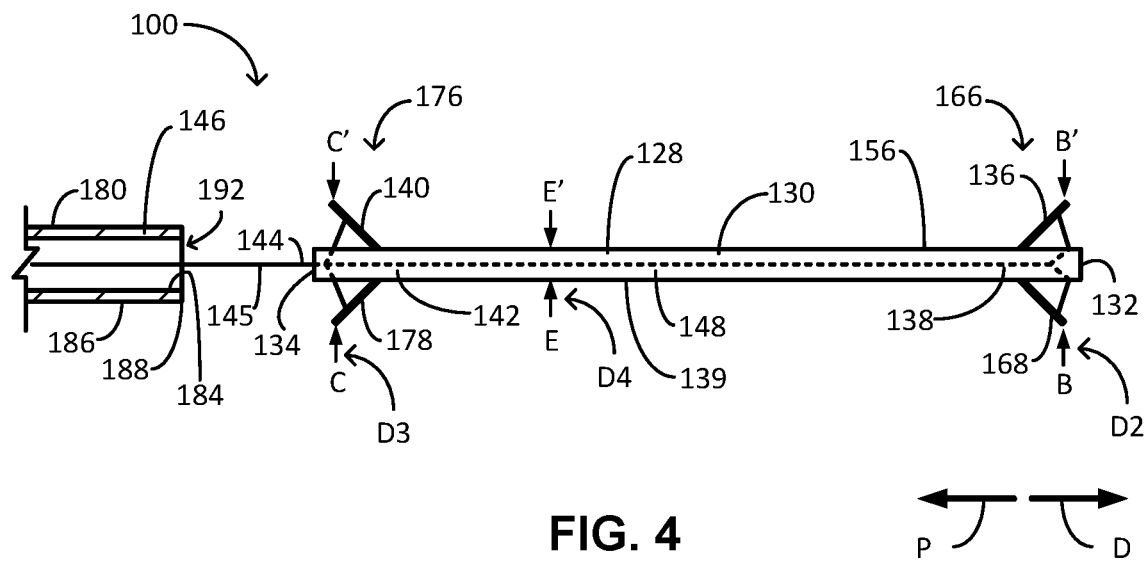
FIG. 4 is a schematic illustration of the medical system of FIGS. 1-3 with a distal petal and a proximal petal extending from the stent.

FIG. 4 schematically illustrates medical system 100 with sheath 146 proximally withdrawn (e.g., in the proximal direction P) relative to stent 128. Stent 128 has translated distally (e.g., in the distal direction D) relative to sheath 146 through sheath distal opening 192, such that distal petals 166 and proximal petals 176 are no longer constrained by sheath interior surface 184 (e.g., no longer bound within the outer boundary defined by sheath exterior surface 186). Thus, the resilient biasing of distal petals 166 may cause distal petals 166 (e.g., each of distal petal 136, 168) to displace in a direction away from stent exterior surface 156 to increase a cross-sectional dimension of stent distal portion 138 (e.g., to assume a deployed position). For example, the resilient biasing may cause distal petals 166 to displace in a direction away from stent exterior surface 156 to define a maximum cross-sectional dimension D2 (e.g., a diameter) of stent distal portion 138. The maximum cross-sectional dimension D2 is represented as the displacement between arrow B and arrow B' in FIG. 4. In like manner, the resilient biasing of proximal petals 176 may cause proximal petals 176 (e.g., each of proximal petals 140, 178) to displace in a direction away from stent exterior surface 156 (e.g., to assume a deployed position) to define a maximum cross-sectional dimension D3 (e.g., a diameter) of stent proximal portion 142. The maximum cross-sectional dimension D3 is represented as the displacement between arrow C and arrow C' in FIG. 4.

In examples, the maximum cross-sectional dimension D2 is greater than a maximum cross-sectional diameter D4 of stent medial portion 139, represented as the displacement between arrow E and arrow E' in FIG. 4. In some example, the maximum cross-sectional dimension D2 is greater than maximum cross-sectional dimension D1 of sheath 146. The maximum cross-sectional dimension D4 may be greater than the maximum cross-sectional diameter D3 of stent medial portion 139 and/or the maximum cross-sectional diameter D1 of sheath 146.

Figure 5:
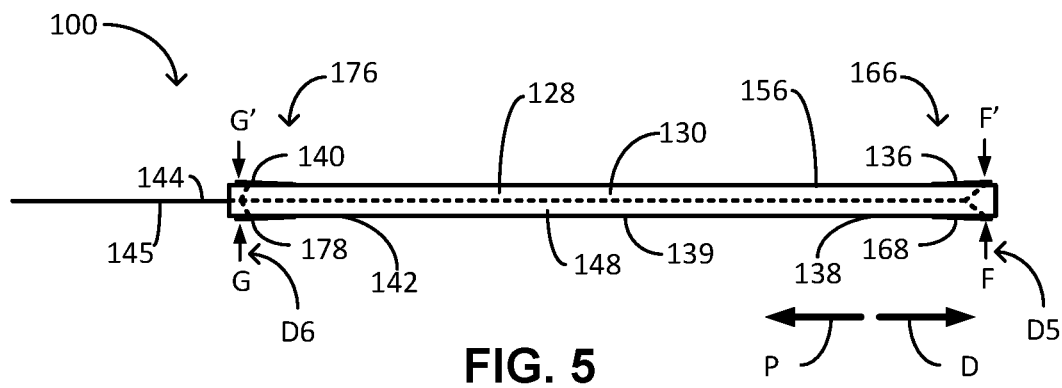
FIG. 5 is a schematic illustration of the medical system of FIGS. 1-4 with a suture mechanically engaged with a distal petal and a proximal petal of the stent.

FIG. 5 schematically illustrates medical system 100 with suture 144 transmitting a proximal force to distal petals 166 and proximal petals 176. The force transmitted to distal petals 166 has caused distal petals 166 to displace toward stent body 130 to decrease a cross-sectional dimension of stent distal portion 138, such that distal petals 166 define a cross-sectional dimension D5 (e.g., a diameter) of stent distal portion 138. The cross-sectional dimension D5 is represented as the displacement between arrow F and arrow F' in FIG. 5. The cross-sectional diameter D5 may be less than the maximum cross-sectional diameter D2 (FIG. 4) and/or the maximum cross-sectional diameter D1 (FIG. 3). The force transmitted to proximal petals 176 has caused proximal petals 176 to displace toward stent body 130 to decrease a cross-sectional dimension of stent proximal portion 142, such that proximal petals 176 define a cross-sectional dimension D6 (e.g., a diameter) of stent proximal portion 142. The cross-sectional dimension D6 is represented as the displacement between arrow G and arrow G' in FIG. 5. The cross-sectional diameter D6 may be less than the maximum cross-sectional diameter D3 (FIG. 4) and/or the maximum cross-sectional diameter D1 (FIG. 3). Stent 128 may be configured such that the cross-sectional dimension D5 and the cross-sectional dimension D6 facilitate withdrawal (e.g., by a clinician) of stent 128 through ureter 110, bladder 112, and urethra 124 of patient 104 (FIG. 1).

Figure 6:
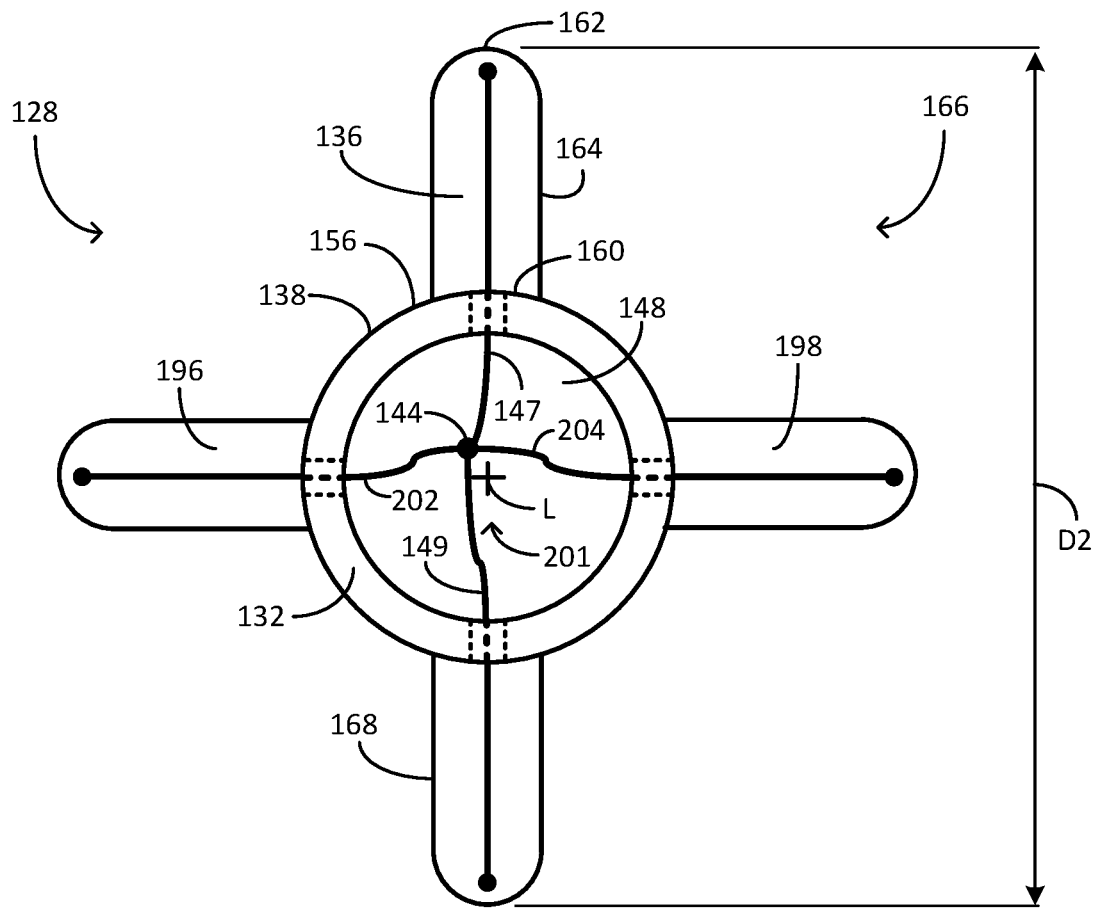
FIG. 6 is a schematic end view of the medical system of FIGS. 1-5 with a plurality of distal petals extending from a sheath body.

As discussed, stent 128 may include any number of distal petals within distal petals 166. As an example, FIG. 6 illustrates an end view of stent 128 (viewed toward stent distal end 132) including distal petals 166, wherein distal petals 166 include distal petal 136, distal petal 168, a distal petal 196, and a distal petal 198. Longitudinal axis L extends out of the page through stent lumen 148. Suture 144 extends through stent lumen 148 and includes a plurality of suture distal portions 201, including suture distal portion 147 mechanically engaged with distal petal 136, suture distal portion 149 mechanically engaged with distal petal 168, a suture distal portion 202 mechanically engaged with distal petal 196, and a suture distal portion 204 mechanically engaged with distal petal 198. Distal petal 136 and distal petal 168 extend away from stent exterior surface 156 to define maximum cross-sectional dimension D2. Distal petal 196 and distal petal 198 also extend away from stent exterior surface 156 and may define a cross-sectional dimension of stent distal portion 138 similar to maximum cross-sectional dimension D2.

Distal petals 166 may be angularly displaced around stent lumen 148 such that a first distal petal (e.g., distal petal 136) and a second distal petal (e.g., distal petal 196) define an angular displacement between the first distal petal and the second distal petal. For example, FIG. 6 illustrates an angular displacement between distal petal 136 and distal petal 196 of about 90 degrees, however the first distal petal and the second distal petal may define any angular displacement. In some examples, distal petals 166 are arranged substantially symmetrically around stent lumen 148, such that each distal petal defines a substantially equal angular displacement with a circumferentially adjacent distal petal, however this is not required. A given distal petal (e.g., distal petal 136) may define an angular displacement with a first circumferentially adjacent distal petal (e.g., distal petal 196) that is greater than or less than an angular displacement defined with a second circumferentially adjacent petal (e.g., distal petal 198).

In examples, distal petals 166 include at least a first distal petal (e.g., distal petal 136) and a second distal petal (e.g., distal petal 168), and the first distal petal is resiliently biased to extend away and/or displace from stent exterior surface 156 in a first direction and the second distal petal is resiliently biased to extend away and/or displace from exterior surface 156 in a second direction different from the first direction. In examples, the first direction defines a first radial direction from longitudinal axis L and the second direction defines a second radial direction from longitudinal axis L.

Figure 7:
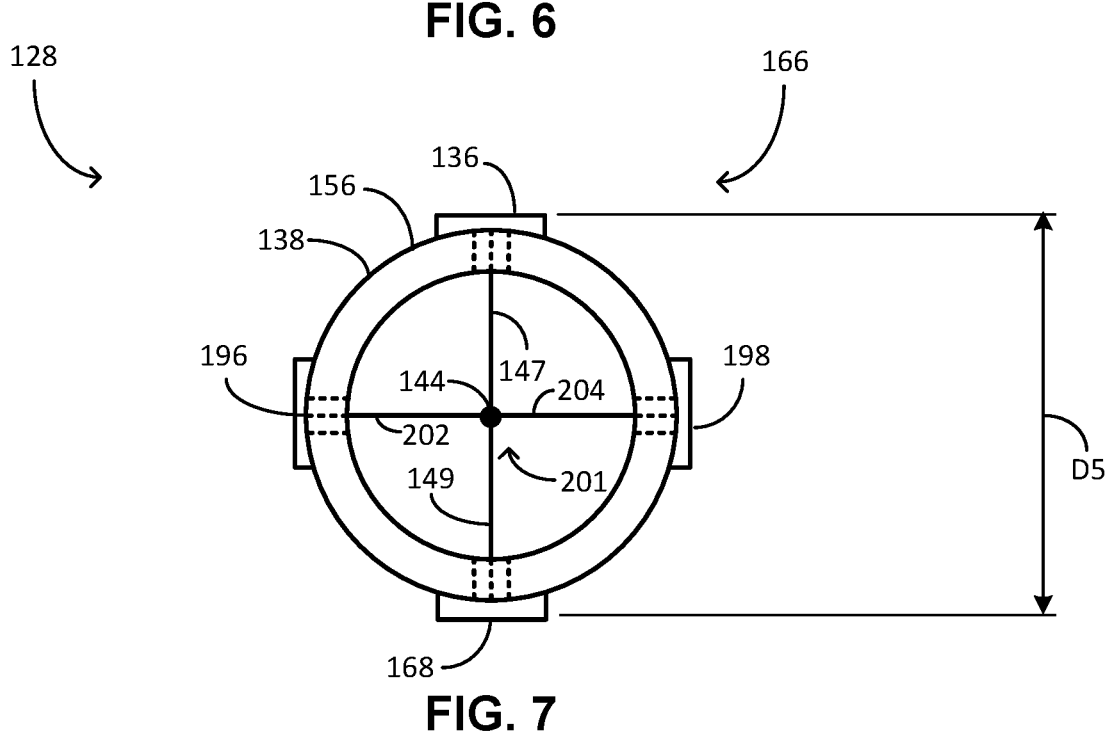
FIG. 7 is a schematic end view of the medical system of FIGS. 1-6 with a plurality of distal petals displaced toward a stent body.

FIG. 7 illustrates suture 144 causing the plurality of suture distal portions 201 to exert inward (e.g., in the direction of longitudinal axis L) forces on distal petals 166, such that distal petals 166 displace toward stent exterior surface 156. Suture 144 transmits a force to cause suture distal portion 147 to exert an inward force on distal petal 136, cause suture distal portion 149 to exert an inward force on distal petal 168, cause suture distal portion 202 to exert an inward force on distal petal 196, and cause suture distal portion 204 to exert an inward force on distal petal 198. Distal petal 136 and distal petal 168 are substantially collapsed such that stent distal portion 138 substantially define cross-sectional dimension D5. Distal petal 196 and distal petal 198 are also substantially collapsed and may define a cross-sectional dimension of stent distal portion 138 similar to cross-sectional dimension D5.

Figure 8:
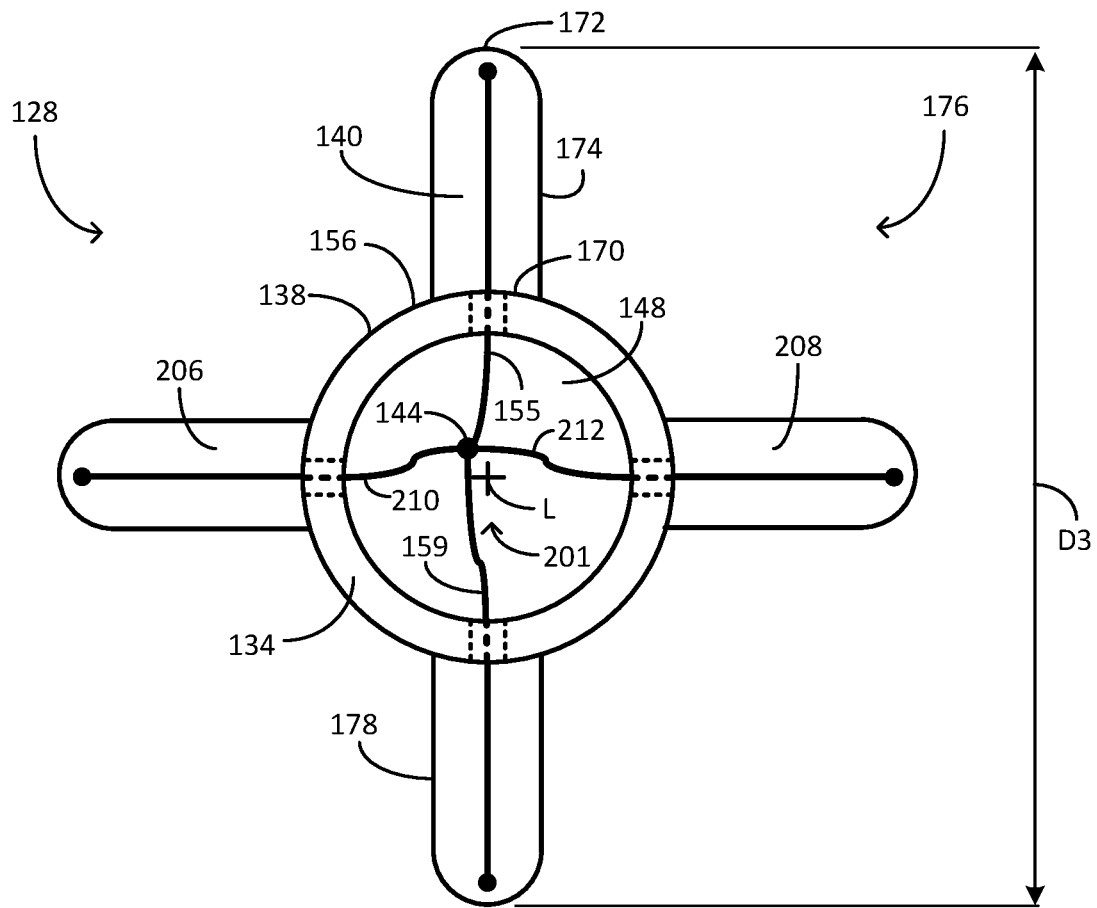
FIG. 8 is a schematic end view of the medical system of FIGS. 1-7 with a plurality of proximal petals extending from a sheath body.
Figure 9:
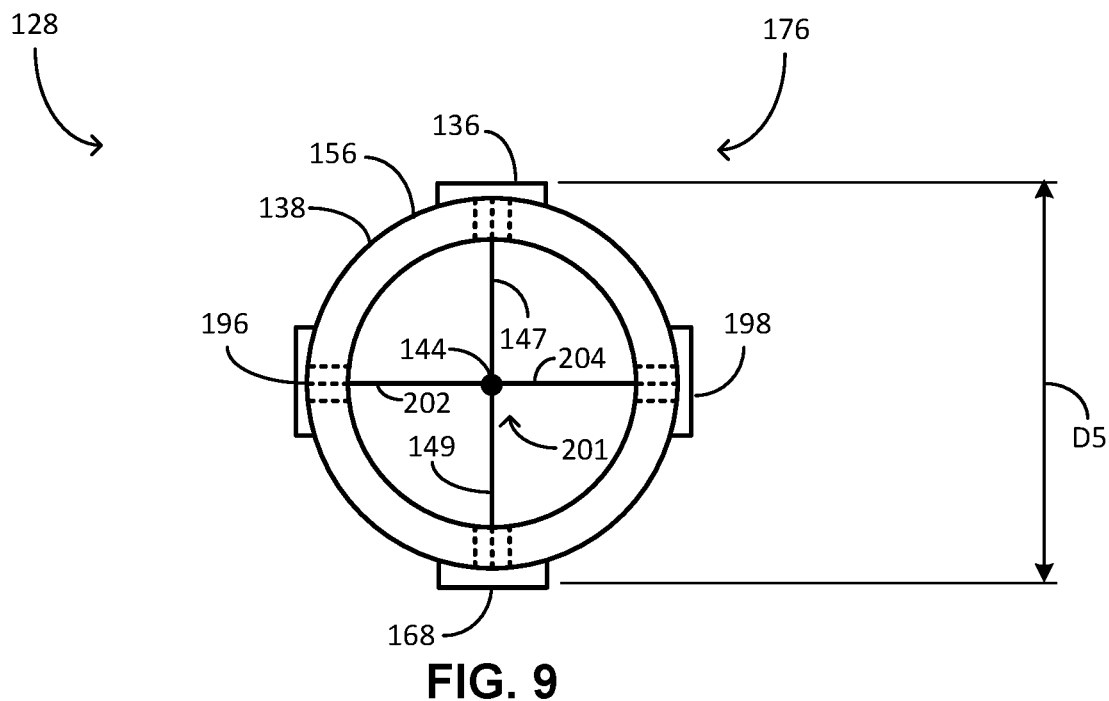
FIG. 9 is a schematic end view of the medical system of FIGS. 1-8 with a plurality of proximal petals displaced toward a stent body.

Stent 128 may include any number of proximal petals within proximal petals 176. As an example, FIG. 8 illustrates an end view of stent 128 (viewed toward stent proximal end 134) including proximal petals 176. Proximal petals 176 include proximal petal 140, proximal petal 178, a proximal petal 206, and a proximal petal 208. Longitudinal axis L extends out of the page through stent lumen 148. Suture 144 extends through stent lumen 148, with plurality of suture distal portions 201 including suture distal portion 155 mechanically engaged with proximal petal 140, suture distal portion 159 mechanically engaged with proximal petal 178, a suture distal portion 210 mechanically engaged with proximal petal 206, and a suture distal portion 212 mechanically engaged with proximal petal 208. Proximal petal 140 and proximal petal 178 extend away from stent exterior surface 156 to define maximum cross-sectional dimension D3. Proximal petal 206 and proximal petal 208 also extend away from stent exterior surface 156 and may define a cross-sectional dimension of stent proximal portion 142 similar to maximum cross-sectional dimension D3.

Proximal petals 176 may be angularly displaced around stent lumen 148 such that a first proximal petal (e.g., proximal petal 140) and a second proximal petal (e.g., proximal petal 206) define an angular displacement between the first distal petal and the second distal petal. For example, FIG. 8 illustrates an angular displacement between proximal petal 140 and proximal petal 206 of about 90 degrees, however the first distal petal and the second distal petal may define any angular displacement. In some examples, proximal petals 176 are arranged substantially symmetrically around stent lumen 148, such that each proximal petal defines a substantially equal angular displacement with a circumferentially adjacent proximal petal, however this is not required. A given proximal petal (e.g., proximal petal 140) may define an angular displacement with a first circumferentially adjacent distal petal (e.g., proximal petal 206) that is greater than or less than an angular displacement defined with a second circumferentially adjacent petal (e.g., proximal petal 208).

In examples, proximal petals 176 include at least a first proximal petal (e.g., proximal petal 140) and a second proximal petal (e.g., proximal petal 178), and the first proximal petal is resiliently biased to extend away and/or displace from stent exterior surface 156 in a primary direction and the second distal petal is resiliently biased to extend away and/or displace from exterior surface 156 in a secondary direction different from the primary direction. In examples, the primary direction defines a primary radial direction from longitudinal axis L and the secondary direction defines a secondary radial direction from longitudinal axis L.

Any of distal petals 166 (e.g., distal petal 136) may be attached to stent body 130 in any manner. For example, distal petal 136 may be substantially unitary with stent body, such that there is a substantial absence of a material interface between distal petal 136 and stent body 130. In other examples, distal petal 136 may attached to stent body using an adhesive, a fastening device, welding, or some other method. Any of proximal petals 176 (e.g., proximal petal 140) may be attached to stent body 130 in any manner. For example, proximal petal 140 may be substantially unitary with stent body, such that there is a substantial absence of a material interface between proximal petal 140 and stent body 130. In other examples, proximal petal 140 may attached to stent body using an adhesive, a fastening device, welding, or some other method. In some examples, some of distal petals 166 and/or proximal petals 176 may be substantially unitary with stent body 130 while others of distal petals 166 and/or proximal petals 176 attached to stent body using an adhesive, a fastening device, welding, or some other method.

FIG. 7 illustrates suture 144 causing the plurality of suture distal portions 201 to exert inward (e.g., in the direction of longitudinal axis L) forces on proximal petals 176, such that proximal petals 176 displace toward stent exterior surface 156. Suture 144 transmits a force to cause suture distal portion 155 to exert an inward force on proximal petal 140, cause suture distal portion 159 to exert an inward force on proximal petal 178, cause suture distal portion 210 to exert an inward force on proximal petal 206, and cause suture distal portion 212 to exert an inward force on proximal petal 208. Proximal petal 140 and proximal petal 178 are substantially collapsed such that stent distal portion 138 substantially define cross-sectional dimension D6. Proximal petal 206 and proximal petal 208 are also substantially collapsed and may define a cross-sectional dimension of stent proximal portion 142 similar to cross-sectional dimension D6.

Figure 10:
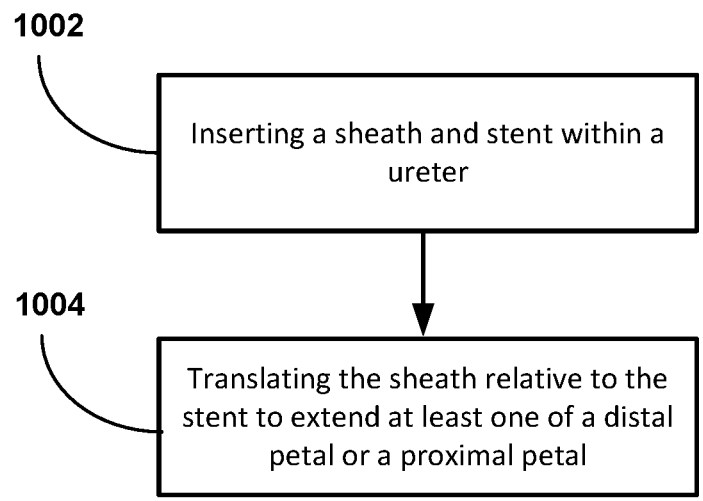
FIG. 10 is a flow diagram of an example technique of using a medical system.

A technique for using a stent is illustrated in FIG. 10. Although the technique is described mainly with reference to stent 128 FIGS. 1-9, the technique may be applied to other stents in other examples.

The technique may include positioning a sheath 146 and a stent 128 within a ureter 110 of patient 104 (1002). The technique may include inserting stent 128 within sheath 146 to cause distal petals 166 and/or proximal petals 176 to displace inwards towards and/or press against a stent exterior surface 156. The technique may include inserting stent 128 within a sheath lumen 182 defined by sheath 146. A sheath interior surface 184 may exert a force on distal petals 166 and/or proximal petals 176 to cause distal petals 166 and/or proximal petals 176 to displace inwards towards and/or press against stent exterior surface 156. In examples, sheath interior surface 184 overcomes the resilient biasing of distal petals 166 and/or proximal petals 176 to cause distal petals 166 and/or proximal petals 176 to displace inwards towards and/or press against stent exterior surface 156. In examples, sheath 146 bounds stent 128 within an outer boundary defined by a sheath exterior surface 186 when stent 128 inserts within sheath lumen 182. Sheath 146 may position stent 128 within ureter 110 when sheath 146 is positioned in ureter 110 (e.g., by a physician) when stent 128 is inserted in sheath lumen 182.

The technique may include translating sheath 146 relative to stent 128 to cause distal petals 166 and/or proximal petals 176 to extend (e.g., establish a deployed position) (1004). In examples, sheath 146 may translate proximally relative to stent 128 to cause distal petals 166 and/or proximal petals 176 to extend. At least some portion of stent 128 may pass through a sheath distal opening 192 when sheath 146 translates proximally relative to stent 128.

The technique may include extending distal petal 136 attached to a distal portion 138 of a stent body 130 of stent 128. Stent body 130 may be configured to be positioned within ureter 110 of patient 104. Stent body 130 may be configured such that distal portion 138 substantially positions within kidney 108 of patient 104 when a proximal portion 142 of stent body 130 positioned substantially within bladder 112 of patient 104. Stent body 130 may be configured such that a stent medial portion 139 between stent distal portion 138 and stent proximal portion 142 positions within ureter 110 when distal portion 138 substantially positions within kidney 108 and/or proximal portion 142 substantially positions within bladder 112.

In examples, distal petal 136 includes a distal petal fixed end 160 secured to stent body 130 and a distal petal free end 162 opposite distal petal fixed end 160, and distal petal free end 162 displaces in a direction away from stent body 130 when distal petal 136 extends. Distal petal free end 162 may displace in a direction substantially perpendicular to a longitudinal axis L extending through a stent lumen 148 of stent 128. In examples, distal petal 136 is resiliently biased, and the resilient biasing of distal petal 136 causes distal petal 136 to extend in a direction away from stent body 130 when distal petal 136 extends.

The technique may include resisting a proximal translation of stent 128 using extended distal petal 136. Distal petal 136 may engage an anatomical structure of patient 104 to resist the proximal translation. In examples, stent 128 includes a plurality of distal petals 166 including distal petal 136 and other distal petals, and the other distal petals extend away from stent body 130 when distal petal 136 extends away from stent body 130. In examples, distal petals 166 extend to define maximum cross-sectional dimension D2. Stent body 130 may be configured such that distal petals 166 substantially position within kidney 108 of patient 104 when proximal portion 142 positions substantially within bladder 112 of patient 104. One or more of the other distal petals may resist the proximal translation of stent 128 when distal petal 136 resists the proximal translation of stent 128. One or more of the other distal petals may engage an anatomical structure of patient 104 to resist the proximal translation.

The technique may include extending a proximal petal 140 attached to proximal portion 142 of stent body 130. In examples, proximal petal 140 includes a proximal petal fixed end 170 secured to stent body 130 and a proximal petal free end 172 opposite proximal petal fixed end 170, and proximal petal free end 172 displaces in a direction away from stent body 130 when proximal petal 140 extends. Proximal petal free end 172 may displace in a direction substantially perpendicular to a longitudinal axis L. In examples, proximal petal 140 is resiliently biased, and the resilient biasing of proximal petal 140 causes proximal petal 140 to extend in a direction away from stent body 130 when proximal petal 140 extends.

The technique may include resisting a distal translation of stent 128 using extended proximal petal 140. Proximal petal 140 may engage an anatomical structure of patient 104 to resist the distal translation. In examples, stent 128 includes a plurality of proximal petals 176 including proximal petal 140 and other proximal petals, and the other distal proximal petals extend away from stent body 130 when proximal petal 136 extends away from stent body 130. In examples, proximal petals 176 extend to define maximum cross-sectional dimension D3. Stent body 130 may be configured such that proximal petals 176 substantially position within bladder 112 of patient 104 when distal portion 138 positions substantially within kidney 108 of patient 104. One or more of the other proximal petals may resist the distal translation of stent 128 when proximal petal 140 resists the distal translation of stent 128. One or more of the other distal petals may engage an anatomical structure of patient 104 to resist the distal translation.

The technique may include causing distal petals 166 and/or proximal petals 176 to displace toward stent exterior surface 156 of stent body 130 using suture 144. Suture 144 may transmit a force (e.g., a proximal force) exerted on suture proximal portion 145 (e.g., by a clinician) to distal petal 136 and/or proximal petal 140 to cause distal petal 136 and/or proximal petal 140 to displace toward stent exterior surface 156. In examples, suture 144 includes a plurality of distal suture ends 201 and suture 144 transmits a force from suture proximal portion 145 to each distal suture end in the plurality of distal suture ends 201. Each distal suture end in the plurality of distal suture ends 201 may transmit the force to at least one of distal petals 166 and/or proximal petals 176. In examples, suture proximal portion 145 receives a single force (e.g., a proximal force), and suture 144 transmits a portion of the single force to each suture distal portion to cause distal petals 166 and proximal petals 176 to displace toward stent exterior surface 156. In examples, distal petals 166 define cross-sectional dimension D5 when suture 144 causes distal petals 166 to displace toward stent exterior surface 156. In examples, proximal petals 176 define cross-sectional dimension D6 when suture 144 causes proximal petals 176 to displace toward stent exterior surface 156.

The present disclosure includes the following examples.

Example 1: A medical system including a stent, the stent comprising: a stent body defining a distal end and a proximal end, wherein the stent body is configured to be positioned in a ureter of a patient when the distal end is positioned substantially in a kidney of a patient and the proximal end is positioned substantially in a bladder of the patient; at least one distant petal attached to a distal portion of the stent body, wherein the at least one distal petal is resiliently biased to cause a portion of the at least one distal petal to displace away from an exterior surface of the stent body; and at least one proximal petal attached to a proximal portion of the stent body, wherein the at least one proximal petal is resiliently biased to cause a portion of the at least one proximal petal to displace away from the exterior surface of the stent body.

Example 2: The medical system of example 1, wherein the at least one distal petal is configured to cause the portion of the at least one distal petal to displace toward the exterior surface when a suture exerts a force toward the exterior surface on the portion of the at least one distal petal.

Example 3: The medical system of example 1 or example 2, wherein the at least one proximal petal is configured to cause the portion of the at least one proximal petal to displace toward the exterior surface when a suture exerts a force toward the exterior surface on the portion of the at least one distal petal.

Example 4: The medical system of any of examples 1-3, wherein the at least one distal petal is configured to be positioned substantially in the kidney when the distal end is positioned substantially in the kidney.

Example 5: The medical system of any of examples 1-4, wherein the at least one proximal petal is configured to be positioned substantially in the bladder when the proximal end is positioned substantially in the bladder.

Example 6: The medical system of any of examples 1-5, wherein the stent body defines a proximal opening at the proximal end, a distal opening at the distal end, and a lumen extending from the proximal opening to the distal opening.

Example 7: The medical system of example 6, wherein the stent body includes a stent wall defining the lumen, wherein the stent wall defines suture passage configured to allow a suture to pass from the lumen to mechanically engage with the at least one of distal petal or the at least one proximal petal.

Example 8: The medical system of any of examples 1-7, wherein the at least one distal petal includes a first distal petal and a second distal petal, wherein the first distal petal is resiliently biased to extend away from the exterior surface in a first direction and the second distal petal is resiliently biased to extend away from the exterior surface in a second direction different from the first direction.

Example 9: The medical system of any of examples 1-8, wherein the at least one proximal petal includes a first proximal petal and a second proximal petal, wherein the first proximal petal is resiliently biased to extend away from the exterior surface in a first direction and the second proximal petal is resiliently biased to extend away from the exterior surface in a second direction different from the first direction.

Example 10: The medical system of any of examples 1-9, wherein: the at least one distal petal is configured engage a first anatomical structure to resist a proximal translation of the stent body in the ureter when the stent body is positioned in the ureter and the distal end is in the kidney, and the at least one proximal petal is configured to engage a second anatomical structure to resist a distal translation of the stent body in the ureter when the stent body is positioned in the ureter and the proximal end is in the bladder.

Example 11: The medical system of any of examples 1-10, further comprising a suture extending from the stent body, wherein the suture is configured to cause at least one of the portion of the at least one distal petal or the portion of the at least one proximal petal to displace toward the exterior surface of the stent body when a proximal force is exerted on the suture.

Example 12: The medical system of example 11, wherein the suture extends from the proximal opening.

Example 13: The medical system of example 11 or example 12, wherein the suture defines a plurality of distal ends, wherein a first distal end is secured to the at least one distal petal and a second distal end is secured to the at least one proximal petal.

Example 14: The medical system of example 13, wherein the at least one distal petal includes a plurality of distal petals and the at least one proximal petal includes a plurality of proximal petals, wherein each of the plurality of distal petals and each of the plurality of proximal petals are secured to at least one of the distal ends of the suture.

Example 15: The medical system of any of examples 1-14, further comprising a sheath defining a sheath lumen configured to surround the stent body, wherein the sheath is configured to be positioned in the ureter of a patient when the sheath lumen surrounds the stent body, and wherein the sheath is configured to displace the at least one distal petal and the at least one proximal petal toward the exterior surface when the sheath lumen surrounds the stent body.

Example 16: A medical system including a stent, the stent comprising: a stent body defining a distal end and a proximal end, wherein the stent body is configured to be positioned in a ureter of a patient when the distal end positions substantially in a kidney of a patient and the proximal end positions substantially in a bladder of the patient, and wherein the stent body defines a proximal opening at the proximal end, a distal opening at the distal end, and a lumen extending from the proximal opening to the distal opening; at least one distant petal attached to a distal portion of the stent body, wherein the at least one distal petal is resiliently biased to cause a free end of the at least one distal petal to displace away from an exterior surface of the stent body, and wherein the at least one distal petal is configured to position substantially in the kidney when the distal end positions substantially in the kidney; and at least one proximal petal attached to a proximal portion of the stent body, wherein the at least one distal petal is resiliently biased to cause a free end of the at least one proximal petal to displace away from the exterior surface of the stent body, and wherein the at least one proximal petal is configured to position substantially in the bladder when the proximal end positions substantially in the bladder.

Example 17: The medical system of example 16, wherein: the at least one distal petal is configured to cause the free end of the at least one distal petal to displace toward the exterior surface when a suture exerts a first proximal force on the free end of the at least one distal petal, and the at least one proximal petal is configured to cause the free end of the at least one proximal petal to displace toward the exterior surface when the suture exerts a second proximal force on the free end of the at least one distal petal.

Example 18: The medical system of example 16 or example 17, further comprising a suture extending from the stent body, wherein the suture is configured to cause at least one of the free end of the at least one distal petal or the free end of the at least one proximal petal to displace toward the exterior surface of the stent body when a proximal force is exerted on the suture.

Example 19: A method, comprising: positioning a distal portion of a stent body of a stent and causing at least one distal petal attached to the distal portion to extend by using a resilient biasing of the at least one distal petal, wherein the resilient biasing causes a portion of the at least one distal petal to displace away from an exterior surface of the stent body, and wherein the stent body is configured to be positioned in a ureter of a patient when a distal end of the stent body positions substantially in a kidney of the patient and a proximal end of the stent body positions substantially in a bladder of the patient; and positioning a proximal portion of the stent body and causing at least one proximal petal attached to the proximal portion to extend by using a resilient biasing of the at least one proximal petal, wherein the resilient biasing causes a portion of the at least one proximal petal to displace away from the exterior surface of the stent body.

Example 20: The method of example 19, further comprising translating a sheath surrounding the stent relative to the stent to cause the at least one distal petal to extend and cause the at least one proximal petal to extend.

Various examples of the disclosure have been described. Any combination of the described systems, operations, or functions is contemplated. These and other examples are within the scope of the following claims.

What is claimed is:

1. A medical system including a stent, the stent comprising:
    a stent body defining a distal end and a proximal end, wherein the stent body is configured to be positioned in a ureter of a patient when the distal end is positioned substantially in a kidney of the patient and the proximal end is positioned substantially in a bladder of the patient;
    at least one distal petal attached to a distal portion of the stent body, wherein a distal petal of the at least one distal petal is resiliently biased to cause a portion of the distal petal to displace away from an exterior surface of the stent body;
    at least one proximal petal attached to a proximal portion of the stent body, wherein a proximal petal of the at least one proximal petal is resiliently biased to cause a portion of the proximal petal to displace away from the exterior surface of the stent body; and
    a suture comprising a first distal portion and a second distal portion, wherein the first distal portion is secured to the distal petal and the second distal portion is secured to the proximal petal, wherein the first distal portion extends distal to the second distal portion, and wherein the suture is configured to cause the distal petal or the proximal petal to displace toward the exterior surface of the stent body when a proximal force is exerted on the suture.

2. The medical system of claim 1, wherein the distal petal is configured to be positioned substantially in the kidney when the distal end is positioned substantially in the kidney.

3. The medical system of claim 1, wherein the proximal petal is configured to be positioned substantially in the bladder when the proximal end is positioned substantially in the bladder.

4. The medical system of claim 1, wherein the stent body defines a proximal opening at the proximal end, a distal opening at the distal end, and a lumen extending from the proximal opening to the distal opening.

5. The medical system of claim 4, wherein the stent body includes a stent wall defining the lumen, wherein the stent wall defines a passage configured to allow the suture to pass from the lumen to secure to the at least one of the distal petal or the proximal petal.

6. The medical system of claim 1, wherein the distal petal is a first distal petal, wherein the at least one distal petal further includes a second distal petal, wherein the first distal petal is resiliently biased to extend away from the exterior surface in a first direction and the second distal petal is resiliently biased to extend away from the exterior surface in a second direction different from the first direction.

7. The medical system of claim 1, wherein the proximal petal is a first proximal petal, wherein the at least one proximal petal further includes a second proximal petal, wherein the first proximal petal is resiliently biased to extend away from the exterior surface in a first direction and the second proximal petal is resiliently biased to extend away from the exterior surface in a second direction different from the first direction.

8. The medical system of claim 1, wherein:
the distal petal is configured to engage a first anatomical structure to resist a proximal translation of the stent body in the ureter when the stent body is positioned in the ureter and the distal end is in the kidney, and
the proximal petal is configured to engage a second anatomical structure to resist a distal translation of the stent body in the ureter when the stent body is positioned in the ureter and the proximal end is in the bladder.

9. The medical system of claim 1, wherein the suture extends from a proximal opening defined by the stent body.

10. The medical system of claim 1, wherein the suture defines a plurality of distal ends, wherein the at least one distal petal includes a plurality of distal petals and the at least one proximal petal includes a plurality of proximal petals, wherein each of the plurality of distal petals and each of the plurality of proximal petals are secured to at least one distal end of the plurality of distal ends.

11. The medical system of claim 1, further comprising a sheath defining a sheath lumen configured to surround the stent body,
wherein the sheath is configured to be positioned in the ureter of a patient when the sheath lumen surrounds the stent body, and
wherein the sheath is configured to displace the distal petal and the proximal petal toward the exterior surface when the sheath lumen surrounds the stent body.

12. The medical system of claim 1,
wherein the distal petal includes a distal petal fixed end attached to the distal portion of the stent body and a distal petal free end opposite the distal petal fixed end,
wherein the distal petal is resiliently biased to displace the distal petal free end distal to the distal petal fixed end when the distal petal causes the portion of the distal petal to displace away from the exterior surface of the stent body.

13. The medical system of claim 1,
wherein the proximal petal includes a proximal petal fixed end attached to the proximal portion of the stent body and a proximal petal free end opposite the proximal petal fixed end, and
wherein the proximal petal is resiliently biased to displace the proximal petal free end proximal to the proximal petal fixed end when the proximal petal causes the portion of the proximal petal to displace away from the exterior surface of the stent body.

14. The medical system of claim 5, wherein at least one of:
the distal petal includes a distal petal fixed end attached to the distal portion of the stent body and the suture passage is distal to the distal petal fixed end, or
the proximal petal includes a proximal petal fixed end attached to the proximal portion of the stent body and the suture passage is proximal to the proximal petal fixed end.

15. A medical system including a stent, the stent comprising: a stent body defining a distal end and a proximal end, wherein the stent body is configured to be positioned in a ureter of a patient when the distal end positions substantially in a kidney of a patient and the proximal end positions substantially in a bladder of the patient, and wherein the stent body defines a proximal opening at the proximal end, a distal opening at the distal end, and a lumen extending from the proximal opening to the distal opening; at least one distal petal attached to a distal portion of the stent body, wherein the at least one distal petal is resiliently biased to cause a free end of the at least one distal petal to displace away from an exterior surface of the stent body, and wherein the at least one distal petal is configured to position substantially in the kidney when the distal end positions substantially in the kidney, and wherein the at least one distal petal is configured to cause the free end of the at least one distal petal to displace toward the exterior surface when a suture exerts a first proximal force on the free end of the at least one distal petal; and at least one proximal petal attached to a proximal portion of the stent body, wherein the at least one proximal petal is resiliently biased to cause a free end of the at least one proximal petal to displace away from the exterior surface of the stent body, and wherein the at least one proximal petal is configured to position substantially in the bladder when the proximal end positions substantially in the bladder, and wherein the at least one proximal petal is configured to cause the free end of the at least one proximal petal to displace toward the exterior surface when the suture exerts a second proximal force on the free end of the at least one proximal petal.

16. The medical system of claim 15, further comprising the suture extending from the stent body.

17. A method, comprising:
positioning a distal portion of a stent body of a stent and causing at least one distal petal attached to the distal portion to extend by using a resilient biasing of the at least one distal petal, wherein the resilient biasing causes a portion of the at least one distal petal to displace away from an exterior surface of the stent body, and wherein the stent body is configured to be positioned in a ureter of a patient when a distal end of the stent body positions substantially in a kidney of the patient and a proximal end of the stent body positions substantially in a bladder of the patient;
positioning a proximal portion of the stent body and causing at least one proximal petal attached to the proximal portion to extend by using a resilient biasing of the at least one proximal petal, wherein the resilient biasing causes a portion of the at least one proximal petal to displace away from the exterior surface of the stent body; and
displacing, using a suture, at least one of a distal petal of the at least one distal petal or a proximal petal of the at least one proximal petal toward the exterior surface of the stent body using a proximal force exerted on the suture, wherein the suture includes a first distal portion secured to the distal petal and a second distal portion secured to the proximal petal, and wherein the first distal portion extends distal to the second distal portion.

18. The method of claim 17, further comprising translating a sheath surrounding the stent relative to the stent to cause the at least one distal petal to extend and to cause the at least one proximal petal to extend.

19. The medical system of claim 15,
- wherein the distal petal includes a distal petal fixed end attached to the distal portion of the stent body,
- wherein the distal petal is resiliently biased to displace the free end of the distal petal distal to the distal petal fixed end when the distal petal causes the free end of the distal petal to displace away from the exterior surface of the stent body.

20. The medical system of claim 15,
- wherein the at least one proximal petal includes a proximal petal fixed end attached to the proximal portion of the stent body,
- wherein the proximal petal is resiliently biased to displace the free end of the proximal petal distal to the proximal petal fixed end when the proximal petal causes the free end of the proximal petal to displace away from the exterior surface of the stent body.

\* \* \* \* \*